(12) United States Patent
Yu et al.

(10) Patent No.: US 9,133,114 B2
(45) Date of Patent: Sep. 15, 2015

(54) DENDRIMERS AND METHODS OF PREPARING SAME THROUGH PROPORTIONATE BRANCHING

(71) Applicants: UNIVERSITY OF MARYLAND, BALTIMORE, Baltimore, MD (US); UNIVERSITY OF MARYLAND, COLLEGE PARK, College Park, MD (US)

(72) Inventors: Yihua (Bruce) Yu, Ellicott City, MD (US); Xuyi Yue, Gaithersburg, MD (US)

(73) Assignees: UNIVERSITY OF MARYLAND, BALTIMORE, Baltimore, MD (US); UNIVERSITY OF MARYLAND, COLLEGE PARK, Baltimore, MD (US)

(*) Notice: Subject to any disclaimer, the term of this patent is extended or adjusted under 35 U.S.C. 154(b) by 229 days.

(21) Appl. No.: 13/752,482

(22) Filed: Jan. 29, 2013

(65) Prior Publication Data
US 2013/0197271 A1    Aug. 1, 2013

Related U.S. Application Data

(60) Provisional application No. 61/592,858, filed on Jan. 31, 2012.

(51) Int. Cl.
*A61K 51/06* (2006.01)
*C07C 323/12* (2006.01)
*A61K 49/12* (2006.01)

(52) U.S. Cl.
CPC ............. *C07C 323/12* (2013.01); *A61K 49/124* (2013.01); *A61K 51/06* (2013.01)

(58) Field of Classification Search
CPC ..... A61K 49/124; A61K 51/06; C07C 323/12
USPC ............................................ 568/50; 570/124
See application file for complete search history.

(56) References Cited

U.S. PATENT DOCUMENTS 5,780,644 A * 7/1998 Gozzini et al. ................ 548/478

OTHER PUBLICATIONS

Astruc, D. et al. Dendrimers Designed for Functions: From Physical, Photophysical, and Supramolecular Properties to Applications in Sensing, Catalysis, Molecular Electronics, Photonics, and Nanomedicine, *Chem. Rev.* 2010, 110, 1857-1959.
Bryant, L. H., Jr., et al. Synthesis and relaxometry of high-generation (G=5, 7, 9, and 10) PAMAM Dendrimer-DOTA-Gadolinium Chelates, *Magn. Reson. Imaging* 1999, 9, 348-352.
Caminade, A. M., et al. Fluorinated dendrimers, *Curr. Opin. Colloid Interface Sci.* 2003, 8, 282-295.
Cooper, A. I., et al. Extraction of a hydrophilic compound from water into liquid CO2 using dendritic surfactants, *Nature* 1997, 389, 368-371.
Criscione, J. M., et al. Self-assembly of pH-responsive fluorinated dendrimer-based particulates for drug delivery and noninvasive imaging, *Biomaterials* 2009, 30, 3946-3955.
Eloy, C., *Phys. Rev. Lett.* 2011, 107, 258101-1-258101-5.
Franke, D., et al. DAMMIF, a program for rapid *ab-initio* shape determination in small-angle scattering, *J. Appl. Cryst.*, 2009, 42, 342-346.
Fréchet, J. M. J., Functional polymers and dendrimers: reactivity, molecular architecture, and interfacial energy, *Science* 1994, 263, 1710-1715.
Grayson, S. M., et al. Convergent Dendrons and Dendrimers: from Synthesis to Applications, *Chem. Rev.* 2001, 101, 3819-3868.
Jiang, Z.-X., et al. The synthesis of a geminally perfluoro-tert-butylated β-amino acid and its protected forms as a potential pharmacokinetic modulator and reporter for peptide-based pharmaceuticals, *J. Org. Chem.* 2007, 72, 1464-1467.
Jiang, Z.-X., et al. The design and synthesis of highly branched and spherically symmetric fluorinated oils and amphiles, *Tetrahedron* 2007, 63, 3982-3988.
Jiang, Z.-X., et al. Symmetry-Guided Design and Fluorous Synthesis of a Stable and Rapidly Excreted Imaging Tracer for 19F MRI, *Angew. Chem., Int. Ed.* 2009, 48, 4755-4758.
Jiang, Z.-X., et al. Fluorous mixture synthesis of asymmetric dendrimers, *J. Org. Chem.* 2010, 75, 2044-2049.
Kawaguchi, T., et al. Double Exponential Dendrimer Growth, *J. Am. Chem. Soc.* 1995, 117, 2159-2165.
Knapen, J. W., et al. Homogeneous catalysts based on silane dendrimers functionalized with arylnickel(II) complexes, *Nature* 1994, 372, 659-663.
Konarev, P. V., et al. PRIMUS: a Windows PC-based system for small-angle scattering data analysis, *J Appl Cryst.*, 2003, 36, 1277-1282.
Kozin, M. B., et al. Automated matich of high-and low-resolution structural models, *J. Appl. Crystallogr.* 2001, 34, 33-41.
Nemes, A., et al. Greener fluorous chemistry: Convenient preparation of new types of CF3-rich secondary alkyl mesylates and their use for the synthesis of azides, amines, imidazoles and imidazolium salts, *J. Fluorine Chem.* 2010, 131, 1368-1376.
Newkome, G. R., et al. Dendrimers Derived from 1 → 3 Branching Motifs, *Chem. Rev.* 2010, 110, 6338-6442.
Percec, V., et al. Controlling polymer shape through the self-assembly of dendritic side-groups, *Nature* 1998, 391, 161-164.
Percec, V., et al. Self-organization of supramolecular helical dendrimers into complex electronic materials, *Nature* 2002, 419, 384-387.
Sonke, S., et al. Dendrimers in biomedical applications—reflections on the field, *Adv. Drug Delivery Rev.* 2005, 57, 2106-2129.
Svergun, D. I. Determination of the Regularization Parameter in Indirect—Transform method Using Perceptual Criteria. *J. Appl. Crystallogr.* 1992, 25, 495-503.

(Continued)

*Primary Examiner* — Irina S Zemel
*Assistant Examiner* — Jeffrey Lenihan
(74) *Attorney, Agent, or Firm* — Marianne Fuierer; Moore & Van Allen, PLLC

(57) ABSTRACT

The present invention provides for monodispersed dendrimers having a core, branches and periphery ends, wherein the number of branches increases exponentially from the core to the periphery end and the length of the branches increases exponentially from the periphery end to the core, thereby providing for attachment of chemical species at the periphery ends without exhibiting steric hindrance.

18 Claims, 22 Drawing Sheets

(56) References Cited

OTHER PUBLICATIONS

Svergun, D. I., Restoring low resolution structure of biological macromolecules from solution scattering using simulated annealing, *Biophys. J.* 1999, 76, 2879-2886.

Szabó, D., et al. Novel generation ponytails in fluorous chemistry: Syntheses of primary, secondary, and tertiary (nonafluoro-tert-butyloxy)ethyl amines, *J. Fluorine Chem.* 2006, 127, 1496-1504.

Tomalia, D. A., J., In quest of a systematic framework for unifying and defining nanoscience, *J. Nanopart. Res.* 2009, 11, 1251-1310.

Volkov, V. V., et al. Uniqueness of *ab initio* shape determination in small-angle scattering, J. Appl. Cryst., 2003, 36, 860-864.

Whitten, A., et al. Small-Angle Scattering and Neutron Contrast Variation. In: Micro and Nano Technologies in Bioanalysis. New York: Humana, 2009, pp. 307-322.

Wooley, K. L., et al. Hyperbranched macromolecules via a novel double-stage convergent growth approach, J. *Am. Chem. Soc.* 1991, 113, 4252-4261.

Xu, Z., et al. Rapid Construction of Large-size Phenylacetylene Dendrimers up to 12.5 Nanometers in Molecular Diameter, *Angew. Chem., Int. Ed. Engl.* 1993, 32, 1354-1357.

\* cited by examiner

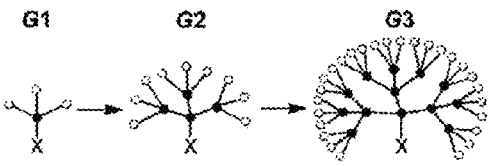
0% proportionate branching: $a = 3$, $b = 1$. For G3,
$(m_0, m_1, m_2, m_3) = (3^0, 3^1, 3^2, 3^3)$, $(l_1, l_2, l_3) = (1^2, 1^1, 1^0)$
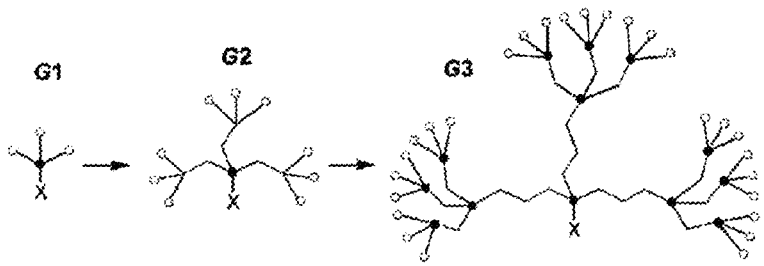
50% proportionate branching: $a = 3$, $b = 2$. For G3,
$(m_0, m_1, m_2, m_3) = (3^0, 3^1, 3^2, 3^3)$, $(l_1, l_2, l_3) = (2^2, 2^1, 2^0)$
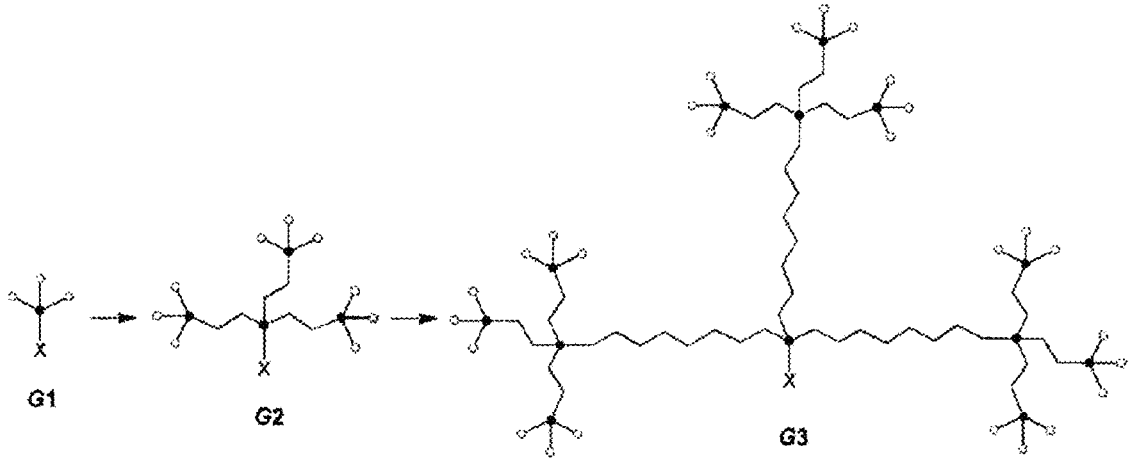
100% proportionate branching: $a = 3$, $b = 3$. For G3,
$(m_0, m_1, m_2, m_3) = (3^0, 3^1, 3^2, 3^3)$, $(l_1, l_2, l_3) = (3^2, 3^1, 3^0)$
Figure 1

*aThe 3→4 step is 75% proportionate branching.

$^a$The 8→16 step is 75% proportionate branching.

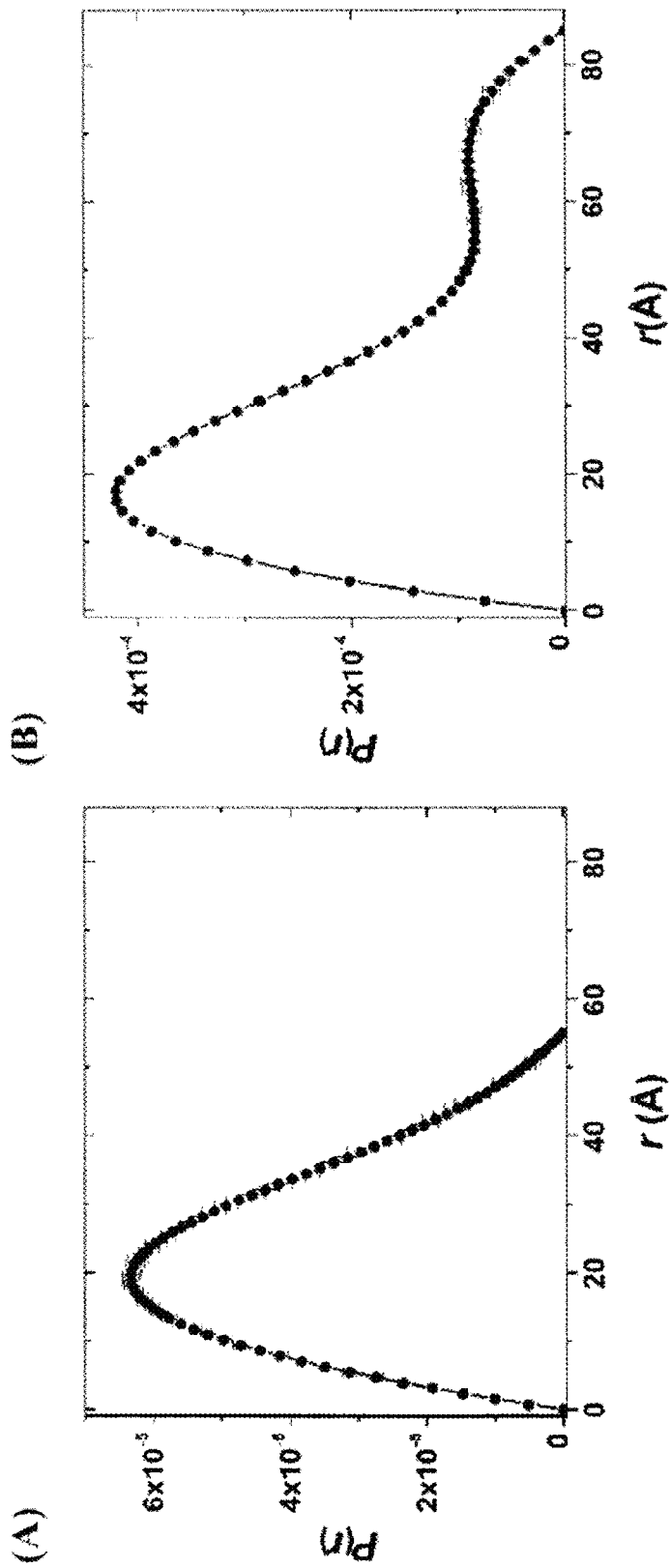
Figure 11 A and B

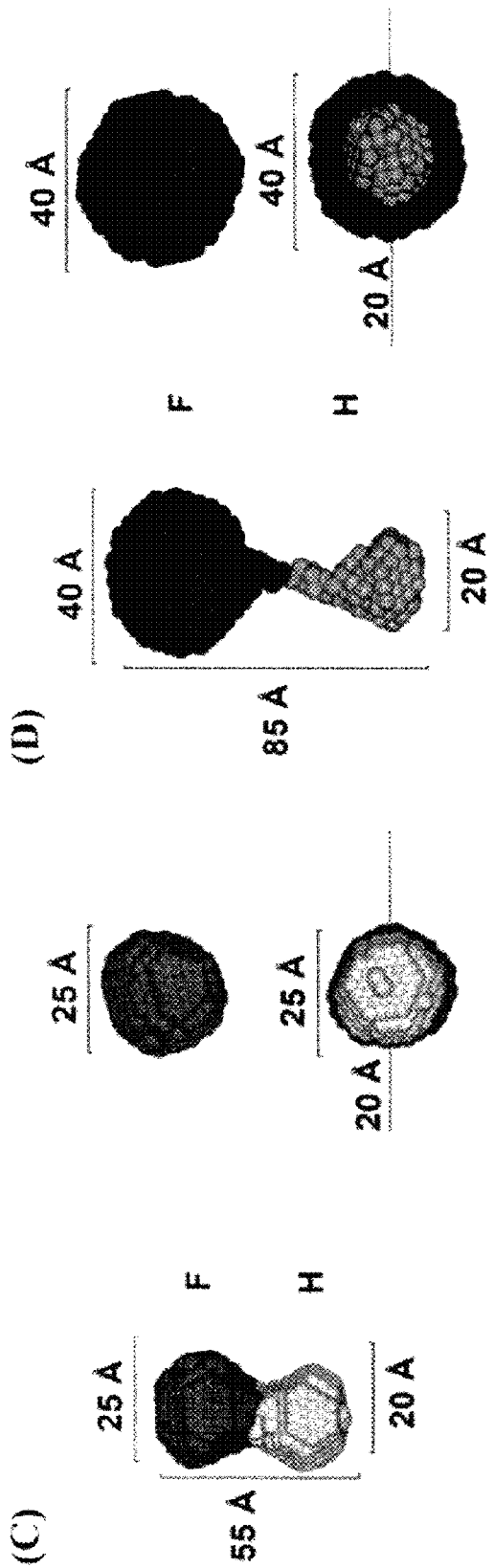
Figure 11 C and D

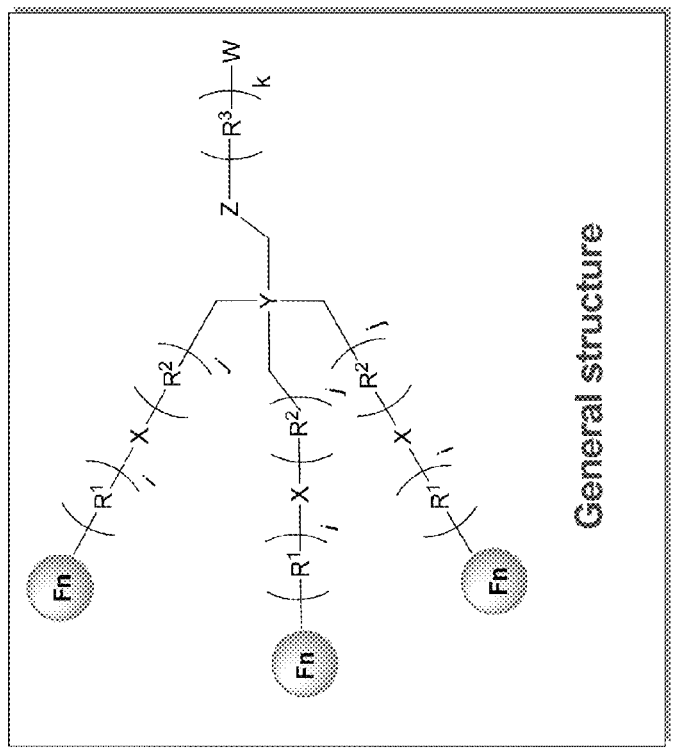
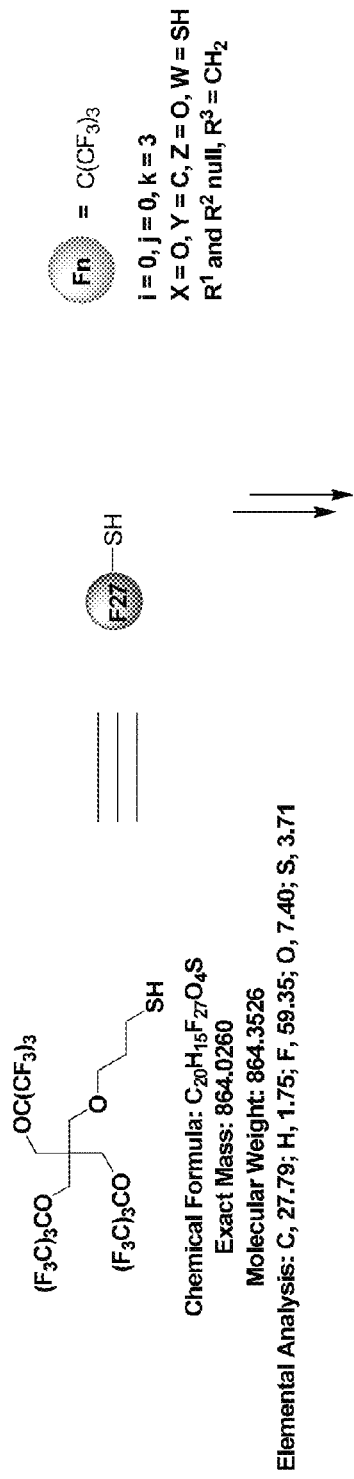
Figure 14A

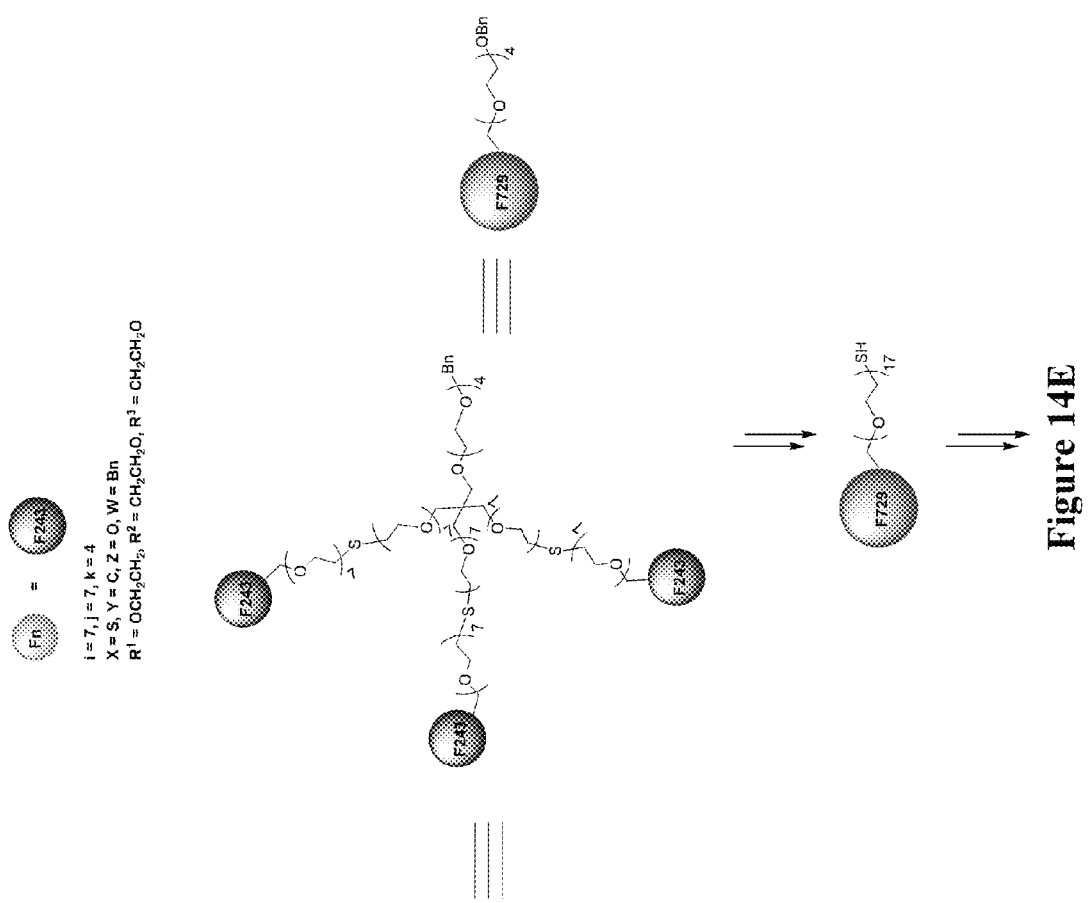

DENDRIMERS AND METHODS OF PREPARING SAME THROUGH PROPORTIONATE BRANCHING

CROSS REFERENCE TO RELATED APPLICATIONS

The application claims priority to U.S. Provisional Application No. 61/592,858, filed on Jan. 31, 2012, the content of which is hereby incorporated by reference herein.

STATEMENT OF GOVERNMENT RIGHTS

This invention was made with government support under Grant Number EB004416 awarded by the National Institutes of Health, Grant Number CBET1133908 awarded by the National Science Foundation and Grant Number DE-FG02-08CH11527 awarded by the Department of Energy. The government has certain rights in the invention.

BACKGROUND OF THE INVENTION

1. Technical Field

The present invention is generally directed toward dendrimers having a core, branches and periphery groups, and more specifically, towards monodispersed dendrimers and method of synthesizing the dendrimers by exponentially increasing the number of branches from the core to the periphery end and exponentially increasing the length of the branches from the periphery end to the core.

2. Related Art

Defect-free synthesis of macromolecules remains a challenge in chemistry, especially for dendrimers, which are finding increased applications in chemistry, materials science, nanotechnology, as well as medicine and pharmacy.(1-7) Dendrimers are tree-like molecules composed of a core ("trunk"), several interior layers ("branches"), and a periphery ("leaves").(8, 9) However, conventional dendrimer design grows dendrimers disproportionately, that being, the number of branches grows exponentially, but the length of branches remains unchanged. The length of branches refers to the number of covalent bonds connecting adjacent branching nodes. Such an unbalanced growth pattern eventually leads to steric congestion and defective dendrimers.(10-14).

Dendrimers reported in the literature have been obtained by two different synthetic approaches: a) divergent synthesis; b) convergent synthesis. The synthesis of most dendrimers has been accomplished using the divergent process. This implies that a polyfunctional molecule is used as a "core" and that, in order to introduce multiplicity, each functional group is bonded to a molecule which also comprises more than one protected reactive site ("propagation monomer"). A first generation dendrimer is thus formed which, by exhaustive addition of polyfunctionalized monomers, gives rise to the next generation and so on. However, monomer protection/deprotection systems need to be used in order to perform the selective modification of specific groups at each synthetic step.

Convergent synthesis, as first proposed by Frechet (8), differs from the divergent approach in that growth starts at what will become the periphery of the macromolecule. Such a method results in the formation of large dendrimeric fragments, which ultimately are attached through a reactive group ("focal point") to a polyfunctional "core". Convergent synthesis has certain advantages over divergent synthesis. With divergent synthesis, the molecule's growth occurs through the simultaneous addition of an increasing number of reactive sites. With the convergent approach, on the other hand, size increase involves a limited number of reactive sites. Convergent synthesis makes use of a smaller excess of reagents. Possible side reactions are therefore avoided and the final products more easily purified.

However, one limitation of the convergent approach is that, as the size of the dendrimers increases, there is an increase in the steric hindrance near the functional group, or focal point, which prevents the group from reacting with the "core." This limitation is also common in divergent synthesis since the size of the molecule increases more slowly than the number of external functional groups. This leads to an increase in steric hindrance around the functional groups which are thus prevented from reacting to give the next generation.

Thus, to overcome the shortcomings of previous and conventional dendrimer synthesis methods including both convergent and divergent, it would be advantageous to provide for dendrimers that avoid the steric congestion caused during the growth of the dendrimer.

SUMMARY OF THE INVENTION

The present invention avoids steric congestion by using a bioinspired strategy called proportionate branching wherein the number of branches and the length of branches in a dendrimer both grow exponentially but in opposite directions, that being, the number of branches grow exponentially from the core to the periphery of a dendrimer and the length of the branches grow exponentially from the periphery to the core.

In one aspect, the present invention provides for a dendrimer comprising a core, branches and periphery ends, wherein length of the branches increases exponentially from the periphery ends to the core and the number of branches increases exponentially from the core to the periphery ends.

In yet another aspect, the present invention provides for a convergent synthesis method for synthesizing a dendrimer comprising functional terminal groups positioned on the periphery ends, wherein the method comprises:

a. reacting the functional terminal groups with first branching units to create first larger units, wherein focal points of these larger units are activated for attachments to second branching units to provide second larger units; and b. repeating such activation and attachment steps until attachment of final branching units to a core thereby completing synthesis of the dendrimer, wherein the second branching units are exponentially longer than the first branching units and each subsequent branching units are exponentially longer than previous branching units.

In a still further aspect, the present invention provides for a method of synthesizing a dendrimer branching structure having a core, branching units and periphery ends, the method comprising proportionate growth of the dendrimer, wherein the number of branches and the length of such branches expand exponentially in opposite directions.

In yet another aspect, the present invention provides for a G-generation dendrimer branching structure having a core, branching units and periphery ends, wherein the number of branches (number of branching nodes) and the length of such branches (number of bonds between nth layer and n−1 layer) expand exponentially in opposite directions with the number of branches increasing exponentially from the core to the periphery ends and the length of the branches increase exponentially from the periphery ends to the core, wherein the number of branches (number of branching nodes) in the nth layer is defined as $m_n$ and the number of bonds between the nth layer and n−1 layer is defined as $l_n$, wherein n is defined as a value of 1≤n≤G, wherein growth of $m_n$ from the core to the periphery is defined by the formula $m_n=a \times m_{n-1}$ and the growth of $l_n$ from the periphery to the core is defined by the formula $l_{n-1}=b \times l_n$, wherein a is the branch multiplicity, having an integer value ranging from 1 to 5, preferably 2, 3 or 4 and that is not changed during the growth of the dendrimer, for growing the number of branches and b is the length multiplier and satisfies 1≤b≤a.

In another aspect, the present invention provides for dendrimers having a predetermined proportionality constant wherein the proportionality constant is defined by the following formula:

$$c = \frac{b-1}{a-1} \times 100\% \tag{1}$$

and a and b are defined above and wherein branch multiplicity a is defined by the number of bonding sites on the branching units and the length multiplier b satisfies 1≤b≤a. Accordingly, the proportionality constant c is at least 2% to 100% and such constant is dependent on the value of a and b. Preferably, the value of b is sufficiently close to the value of a to provide for sequential increases in the $l_n$ values thereby providing for additional bonds to cause an increased length of branches as approaching the core.

In yet another aspect, the present invention provides novel dendrimer complexes as defined herein, wherein the periphery ends may comprise terminal functional groups that are preferably attached to the periphery ends and in some situations may also be internally attached to internal nodes or branches having available binding sites.

Notably the dendrimers of the present invention have a broad range of possible uses including the use in the detection of the presence of various components of a sample, such as, the detection of nucleic acid sequences, antibodies, antigens, immune complexes, pharmaceutical compounds, proteins, or peptides, cell, implants, and thus, applicable in in vitro and in vivo diagnostic methods. The in vivo and in vitro diagnostic procedures which could benefit from the use of dendrimer derivatives are, for example: radioimmunologic assays, electron microscopy, ELISA, X-ray imaging, magnetic resonance imaging (MRI) and immunoscintigraphy.

Another possible use of the dendrimers of the present invention is in the labeling of various compounds. Thus, the present invention further relates to the use of the dendrimers in labeling reactions as well as to labeling kits comprising such dendrimers, wherein the kit further comprises one or more labeling compounds. Suitable labeling compounds/means for labeling include fluorophores, fluorine, biotin, radioisotope labels, enzyme labels, dyes, chemiluminiscence labels, antigens or antibody labels.

Further, the dendrimers of the present invention may be used as delivery devices, that being, transporters of substances, and act as "carriers" for the controlled and targeted release of drugs or other compounds. Examples of such drugs may include but are not limited to antibiotics, analgesic, antihypertensives, radionuclides; signal generators and absorbers; antibodies; metal chelates and hormones. Nucleic acids may also be attached, and thus, the dendrimer may act as a carrier for introduction of nucleic acids into prokaryotic and eukaryotic cells in vitro and in vivo.

Still further, it is possible to prepare dendrimers with a lipophilic interior and a hydrophilic surface thus obtaining molecules that can function as micelles.

In yet another aspect, the present invention provides for a delivery device for the delivery of a therapeutic agent, wherein the delivery device is a dendrimer comprising a generation (G) branching structure comprising a core, branches and periphery ends, wherein length of the branches increases exponentially from the periphery ends to the core and the number of branches increase exponentially from the core to the periphery ends, wherein the therapeutic agent is attached to the periphery ends or enclosed within the branching structure. The therapeutic agent may include, but is not limited to the delivery of antibiotics, analgesic, antibodies; cancer drugs, antiviral, metal chelates, proteins, hormones and nucleic acids.

Other aspects, features and embodiments of the invention will be more fully apparent from the ensuing disclosure and appended claims.

BRIEF DESCRIPTION OF THE FIGURES

FIG. 1 shows the different levels of proportionate branching for G=3 dendrimers. At 100% proportionate branching, $m_1 \times l_1 = m_2 \times l_2 = m_3 \times l_3 = a^G$; i.e., $m_n$ and $l_n$ are inversely proportional to each other for 1≤n≤G, hence the name proportionate branching.

FIG. 11A-D shows pairwise distance distribution functions P(r) for $^{19}$F-81 (A) and $^{19}$F-243 (B) in TFE solution. Side, top, and bottom projections of low-resolution 3D structures of $^{19}$F-81 (C) and $^{19}$F-243 (D). F and H denote, respectively, the fluorocarbon lobe and the hydrophilic lobe.

DETAILED DESCRIPTION OF THE INVENTION

Figure 2:
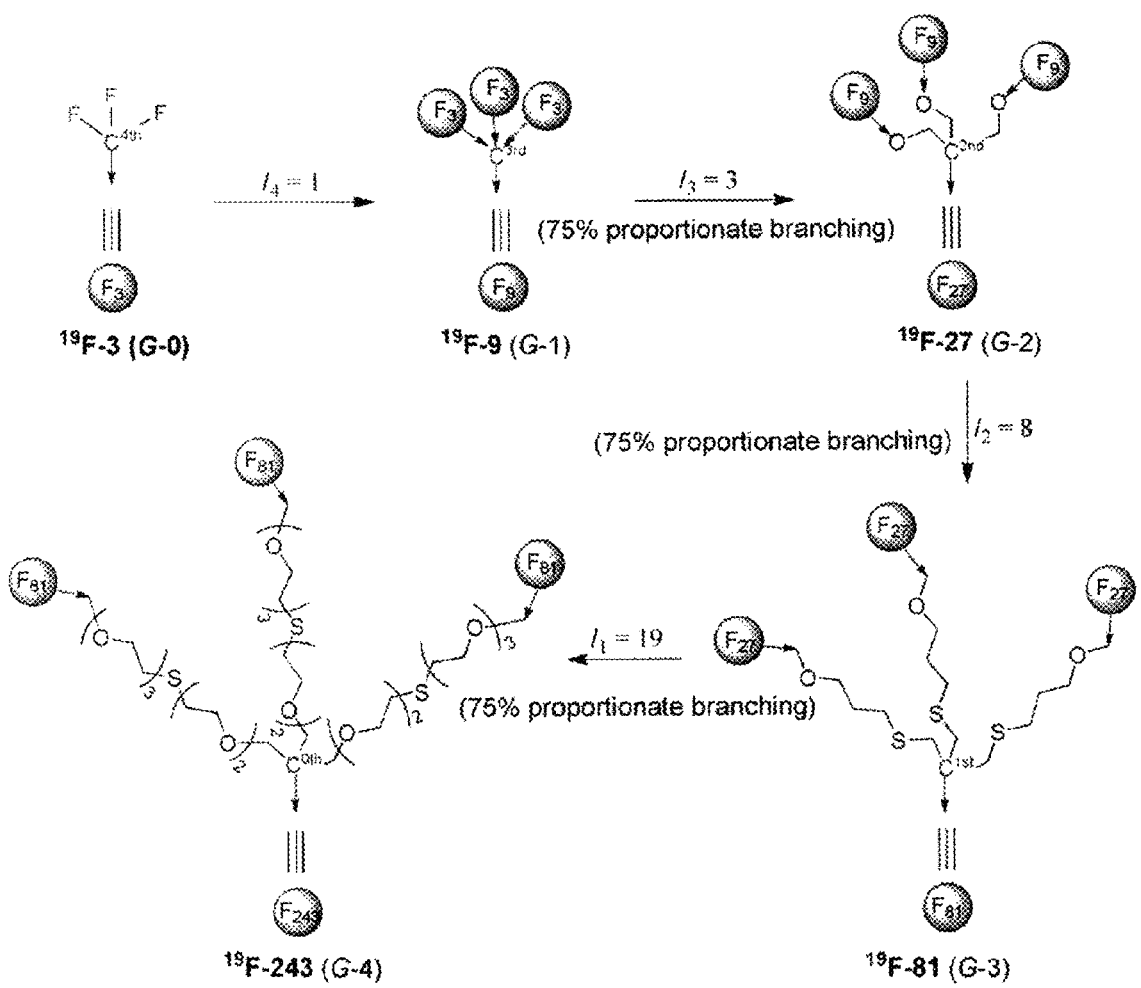
FIG. 2 shows the convergent synthesis of fluorocarbon dendrons at 75% proportionate branching (a=3, b=2.5, c=75%). For the generation 4 dendron, $^{19}$F-243, $(m_0, m_1, m_2, m_3, m_4) = (1, 3, 9, 27, 81)$, $(l_1, l_2, l_3, l_4) = (19, 8, 3, 1)$. The irregularity in $l_n$ values is because b is a non-integer. The calculation of $l_n$ values is given in the synthesis step of that compound.

Making defect-free macromolecules is a challenging issue in chemical synthesis. This challenge is especially pronounced in dendrimer synthesis where exponential growth quickly leads to steric congestion. To overcome this difficulty, proportionate branching in dendrimer growth is disclosed herein wherein the number and the length of branches increase exponentially but in opposite directions. Such a growing process achieves defect-free synthesis of macromolecules.

The present invention provides for proportionate branching which is characterized by a pair of constants, a and b; wherein a is the branch multiplicity for growing the number of branches, and b is the length multiplier for growing the length of branches. For a G-generation dendrimer, the number of branching nodes in the nth layer is denoted as $m_n$, and the number of bonds between the nth and the (n−1)th layer as $l_n$, with $1 \leq n \leq G$. The growth of $m_n$ starts at the core with $m^0 \equiv 1$, and the growth of $l_n$ starts at the periphery with $l_G \equiv 1$. Subsequent growth of $m_n$ and $l_n$, respectively, follows the recursive formulas $m_n = a \times m_{n-1}$ and $l_{n-1} = b \times l_n$. In other words, $m_n$ and $l_n$ both grow exponentially but in opposite directions, with $m_n$ growing from the core to the periphery and $l_n$ growing from the periphery to the core.

Branch multiplicity a is determined by the chemistry of the branching atoms: a=3 for 1→3 connectivity and a=2 for 1→2 connectivity. Length multiplier b satisfies $1 \leq b \leq a$. A proportionality constant c is defined as $$c = \frac{b-1}{a-1} \times 100\% \quad (1)$$

FIG. 1 illustrates three levels of proportionate branching, 0, 50, and 100%. When b=1, c=0%. This is conventional dendrimer growth. When b=a, c=100%. In this case, $m_n \times l_n = a^G$ for $1 \leq n \leq G$. Hence, at 100% proportionate branching, the product of $m_n$ and $l_n$ is a constant. The essence of da Vinci's rule of tree branching is that $m_n \times d_n^2$ is a constant, where $d_n$ is the diameter of branches in the nth layer.(15) Hence, from the trunk to the leaves, the branches of a dendrimer or a tree get proportionately shorter (our rule) or thinner (da Vinci's rule).

Larger b is beneficial for avoiding steric congestion but elevates synthesis difficulty. To strike a balance, it is sensible to allow b to adopt any appropriate value between 1 and a, including non-integers. The idea is that b should be no larger than absolutely necessary. The optimal value of b depends on branch multiplicity and peripheral group. While b can adopt a non-integer value, $l_n$, the number of bonds, cannot. The solution is to let $l_{n-1}$ float between $[bl_n-1, bl_n+1]$. The exact integer value of $l_{n-1}$ depends on the availability of starting materials and the convenience of synthesis, thereby providing the synthetic chemist some flexibility.

Some terms used in this application are as follows:

The term "polymer chain," as used herein, means a molecule built up by the combination of small, relatively simple chemical units, and preferably, forms a linear chain wherein such linear chain may further comprise heteroatoms which are defined as atoms other than carbon.

The term "generation," as used herein, means each successive concentric layer added to the core molecule in the iterative formation of a dendritic structure. The first generation is the monomer layer initially bound to the core molecule while successive generations, for example, the second, third and fourth generations, are bound to the preceding generation. Preferably, the dendrimers of the present invention have at least three generations and range to about 10 generations.

The term "monodispersed," as used herein means dendrimer branching structures of the present invention having at least 95% the same structure and molecular weight (MW), and more preferably, at least 98%, and most preferably at least 99%.

The term "periphery end," as used herein means the outermost generation or the generation furthest from the core molecule. The periphery ends provides a plurality of branches to which the functional terminal moieties may be attached.

The term "branch units," as used herein, means a linear region of a polymer chain that lies between two branch nodes, between a branch node and a terminating functional group, and/or between a branch node and the core.

The term "branch node" as used herein, means an atom to which two or more polymer chains may be attached.

The term "terminal functional group," as used herein, means groups, such as, ester groups, ether groups, thiol groups, carbonyl groups, hydroxyl groups, halogen groups, amide groups, carboxylic groups, and imide groups as well as combinations thereof. In the alternative, such terminal functional groups may include labels (e.g. biotin, fluorophores, fluorine or combinations thereof), drugs, or probe type molecules, as described hereinbelow.

As mentioned in the introductory part of this description, such dense dendrimer structures have several drawbacks, that being, a significant steric hindrance and crowding in the outer layer of the dendrimer, and thus, quenching of fluorophores attached to the outer layers of the dendrimer. In contrast hereto, the dendrimers and dendrimer complexes of the present invention do not possess these drawbacks. As such, the advantages of the dendrimers and dendrimer complexes of the present invention are numerous. They have a sufficiently loose structure to allow conjugation of even quite large entities. Furthermore, the closest neighboring anchoring groups are sufficiently far apart, whereby reduced reactivity, aggregation of the attached entities, fluorescence quenching and other undesirable effects of steric crowding are avoided or minimized. Also, the dendrimers are easily derivatized with a desired entity, e.g. a probe or a labeling compound, whereby the full potential of the multiple sites can be fully exploited, and well-defined conjugates prepared. Furthermore, it is possible to activate the dendrimer in advance, so that chemical modifications of the attached entities are avoided, and naturally occurring functionalities such as amines, carboxylic acids, thiols, alcohols etc. can be brought to react spontaneously with the dendrimer.

In particular, the dendrimer may be heterofunctional. In this way, one type of entity, e.g. a probe or a labeling compound can be attached, either covalently or ionically, to one or more periphery end groups on the dendrimer, while other entities, e.g. other probes or labeling compounds, can be attached to other groups as long as the values of a and b are maintained constant for the predictable exponential growth.

The term "labeling compound," as used herein means a substituent which is useful for detection, that being, suitable for generating a visible or otherwise detectable signal directly or indirectly. In accordance with the present invention, suitable labeling compounds comprise fluorophores, fluorine, biotin, radioisotope labels, enzyme labels, dyes, chemiluminiscence labels, electroluminiscence labels, hapten, antigen or antibody labels. Examples of particular interesting labeling compounds are biotin, fluorescent labels, such as fluorescein labels, e.g. 5-(and 6)-carboxyfluorescein, 5- or 6-carboxyfluorescein, 6-(fluorescein)-5-(and 6)-carboxamido hexanoic acid and fluorescein isothiocyanate, dinitro phenyl radical, rhodamine, tetramethylrhodamine, cyanine dyes such as Cy2, Cy3 and Cy5, optionally substituted coumarin, R-phycoerythrin, allophycoerythrin, Texas Red and Princeston Red as well as conjugates of R-phycoerythrin and, e.g. Cy5 or Texas Red.

The term "probe," as used herein, means a compound of chemical or biological origin that specifically recognizes and binds to markers and/or complexes thereof. Several probes can be envisaged including peptides, nucleic acids, antibodies, antigens, etc.

The core is a single focal point and comprises any organic (aromatic or aliphatic), proteins, amino acids, nucleic acids or inorganic material with at least two available groups for binding with branching units. Branching units may be attached by any of the means known in the chemical field, including nucleophilic, electrophilic, free-radical, and ring opening reactions. Examples of materials containing functional groups that can be used as nucleophiles in nucleophilic reactions are N—H containing materials such as ammonia, amines and polyamines, hydroxyl containing materials such as polyols, polysaccharides, poly(serine), or polyglycerine; thiol containing materials such as polythiols.

The branching units may consist of linear organic (aromatic or aliphatic), proteins, amino acids, nucleic acids or inorganic oligomers or polymers comprising any material which can form oligomers or polymers such as carbon, oxygen, nitrogen, silicon, phosphorous, and the like. The branching units are preferably linear or lightly branched and available for further attachment between two branch nodes, between a branch node and a terminating functional group, and/or between a branch node and the core.

In order to demonstrate the practice of the present invention, the following examples have been prepared and tested as described hereinbelow. The examples should not, however, be viewed as limiting the scope of the invention.

EXAMPLES

Proportionate branching is demonstrated herein by making four generations of fluorocarbon dendrons. The motivation for making fluorocarbon dendrons is to use them as imaging agents for $^{19}$F magnetic resonance imaging (MRI). Fluorine atoms in a fluorinated dendrimer have identical chemical environments, and their $^{19}$F signals coalesce into a single peak for MRI. Defects in fluorinated dendrimers would lead to split $^{19}$F signals, which can create chemical shift image artifacts. Hence, for $^{19}$F MRI applications, defect-free synthesis of fluorinated dendrimers is essential.

Fluorinated asymmetric dendrimers containing 27 fluorine atoms were synthesized and in vivo imaging studies were conducted.(16) Each fluorinated asymmetric dendrimer comprises a fluorocarbon dendron where the branching nodes are carbons with 1→3 connectivity and a hydrophilic dendron where the branching nodes are nitrogens with 1→2 connectivity.(17) Using conventional dendrimer design, the growth of the hydrophilic dendron for 4 generations was conducted without running into steric congestion.(18) However, when attempting to grow the fluorocarbon dendron, steric congestion and incomplete growth were encountered. The fluorocarbon dendron is more prone to steric congestion than the hydrophilic dendron for two reasons: higher branch multiplicity (3 vs 2) and bulkier peripheral group (—CF$_3$ vs —OH).(19) This difficulty with growing dendrons having bulkier peripheral groups provided the incentive for proportionate branching, as described herein.

Using proportionate branching, fluorocarbon dendrons containing 81 and 243 fluorine atoms (peripheral groups), which could not be obtained using conventional methods, were successfully synthesized, by the methods described herein.

Figure 3:
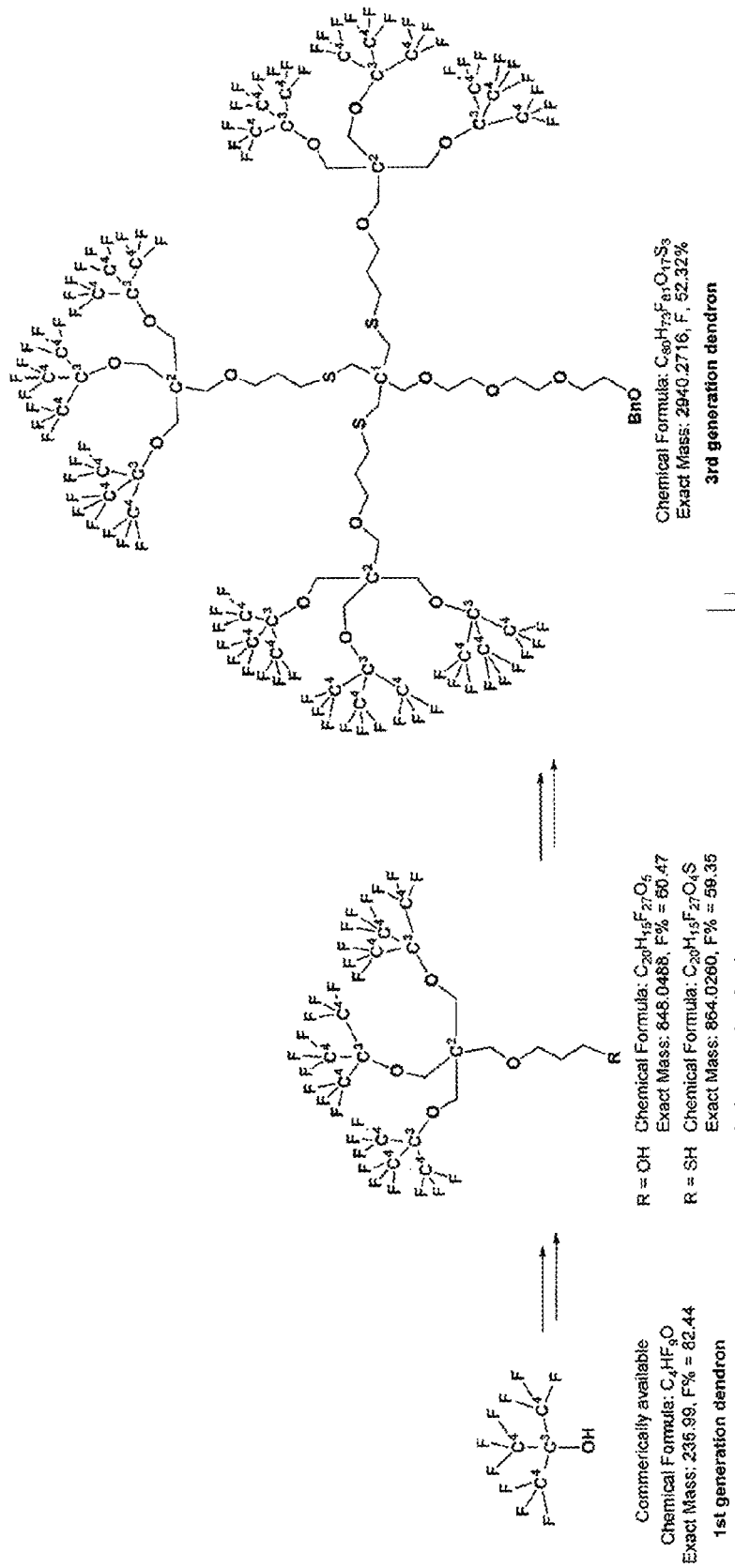
FIG. 3 shows detailed structures of the first three generations of dendrons of FIG. 2.
Figure 4:
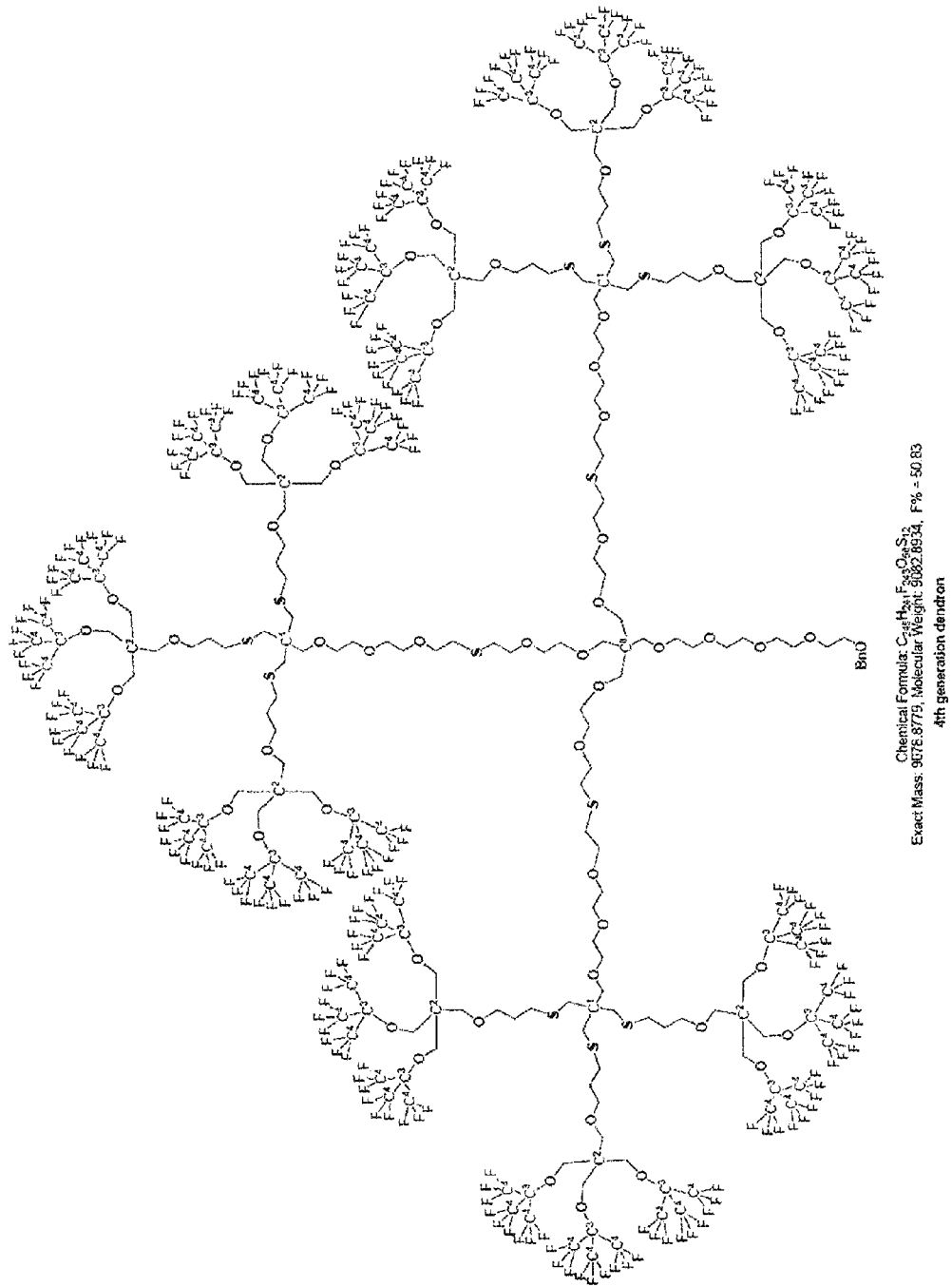
FIG. 4 shows detailed structures of the fourth-generation dendron of FIG. 2 wherein $C^0, C^1, C^2, C^3$ and $C^4$ represent $0^{th}$, $1^{st}$, $3^{rd}$ and $4^{th}$ generation branching point carbon atom and wherein for the $2^{nd}$ generation, R=OH was used for the SAXS experiments.

The results shown herein demonstrate that proportionate branching is an effective strategy to avoid steric congestion in dendrimer synthesis when using bulkier peripheral groups. Using the proportionate branching strategy, a convergent synthesis of four generations of fluorocarbon dendrons was conducted as shown in FIG. 2. For detailed structures of the four fluorocarbon dendrons, see FIGS. 3 and 4. Since all branching atoms are tetrahedron carbons, it is evident that a=3. On the basis of experience with (16, 18, 20, 21) and reported properties of (22, 23) the —CF$_3$ and —C(CF$_3$)$_3$ groups, b was chosen to be b=2.5, hence c=75%. The $l_n$ values are given in FIG. 2.

Figure 5:
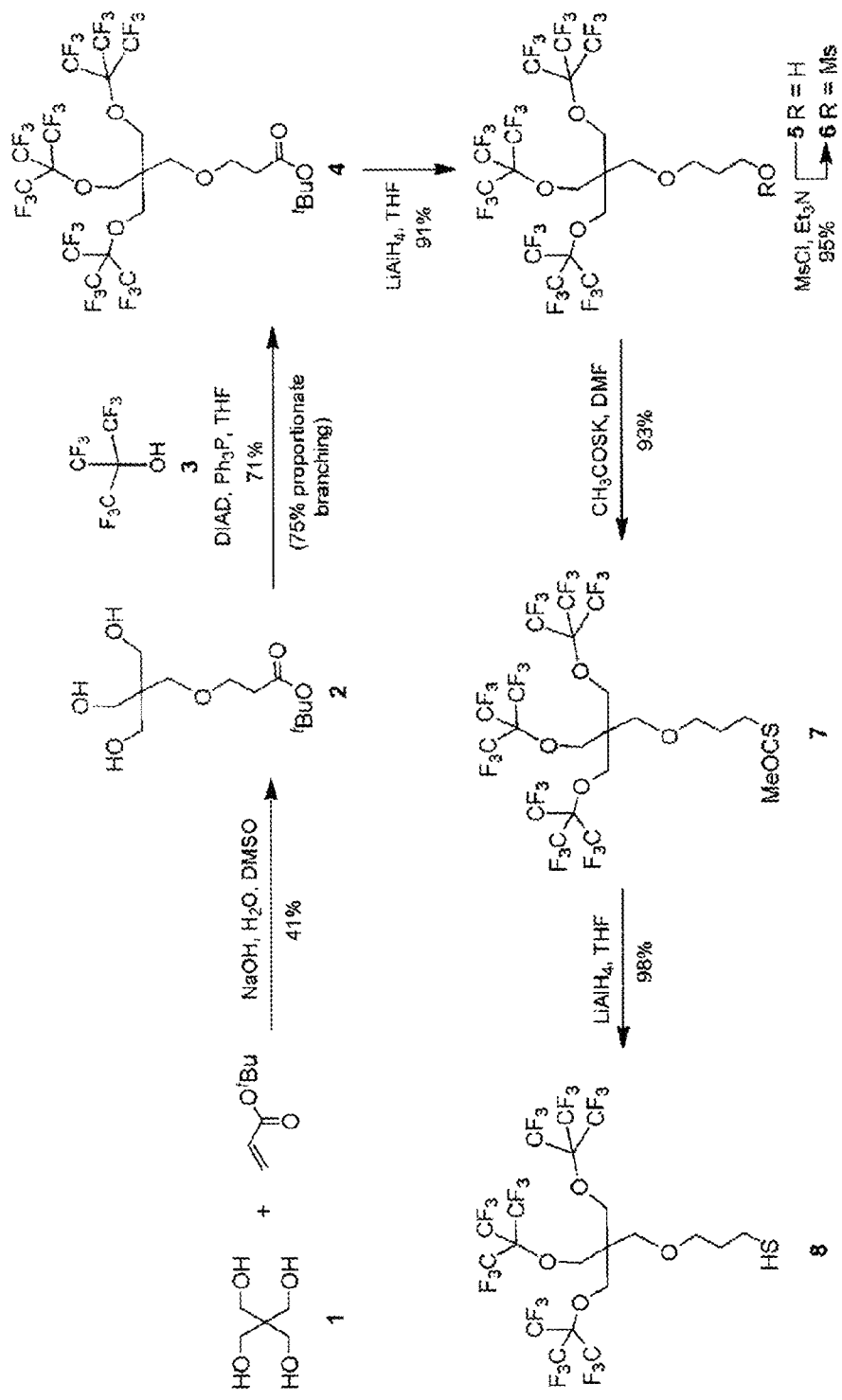
FIG. 5 shows the synthesis of two versions of $^{19}$F-27 (5 and 8)$^a$ wherein 3→4 step is 75% proportionate branching.

To implement the convergent synthesis procedure outlined in FIG. 2, the first-generation dendron, perfluoro-tert-butanol ($^{19}$F-9), is commercially available. Hence the synthesis process starts with making the second-generation dendron $^{19}$F-27 from $^{19}$F-9, as shown in FIG. 5. Pentaerythritol 1, which is commercially available at a low price, was used as the branching unit to ensure a=3. One of the four hydroxyl groups in compound 1 was protected with tert-butyl acrylate to afford compound 2 with a moderate yield. This step also contributes three bonds to $l_2$ (see FIG. 2). Three copies of $^{19}$F-9 (Compound 3) were then grafted onto the remaining three hydroxyl groups in compound 2 using the classic Mitsunobu reaction to give compound 4. The combination of pentaerythritol and the Mitsunobu reaction leads to $l_3$=3, which lies in the range of [2.5×1−1, 2.5×1+1]. This illustrates the principle that the exact integer value of $l_{n-1}$, which lies in the range of [$bl_n$−1, $bl_n$+1], is determined by a combination of starting material and synthesis convenience. From compound 4, reduction of the ester group with LiAlH$_4$ gave the hydroxyl version of $^{19}$F-27 (compound 5). Subsequent mesylation of the primary hydroxyl group in compound 5 afforded mesylate compound 6. Nucleophilic substitution of mesylate compound 6 with potassium thioacetate and then deprotection of the resulting thioester bond in compound 7 afforded the sulfhydryl version of $^{19}$F-27 (compound 8), as shown in FIG. 5.

Figure 6:
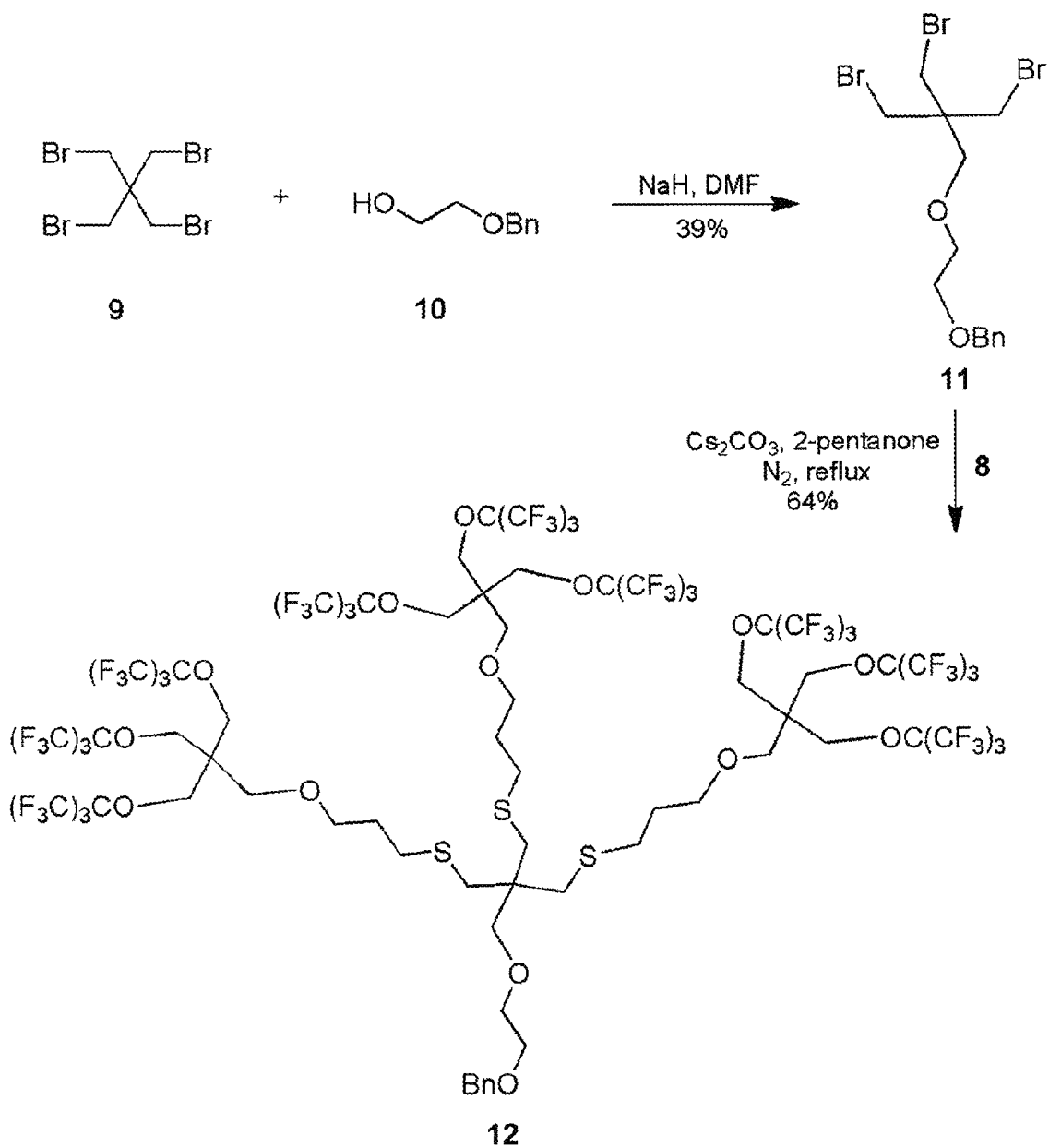
FIG. 6 shows a model reaction for making $^{19}$F-81 compounds.

With $^{19}$F-27 (compound 8) in hand, attention was turned to the synthesis of $^{19}$F-81. Pentaerythritol was used as the branching unit, and grafting $^{19}$F-27 onto pentaerythritol utilized the sulfide bond. Model reactions showed that the reaction between compound 8 and pentaerythritol tribromide proceeded smoothly under a Cs$_2$CO$_3$/2-pentanone condition after various trials, as shown in FIG. 6.

Figure 7:
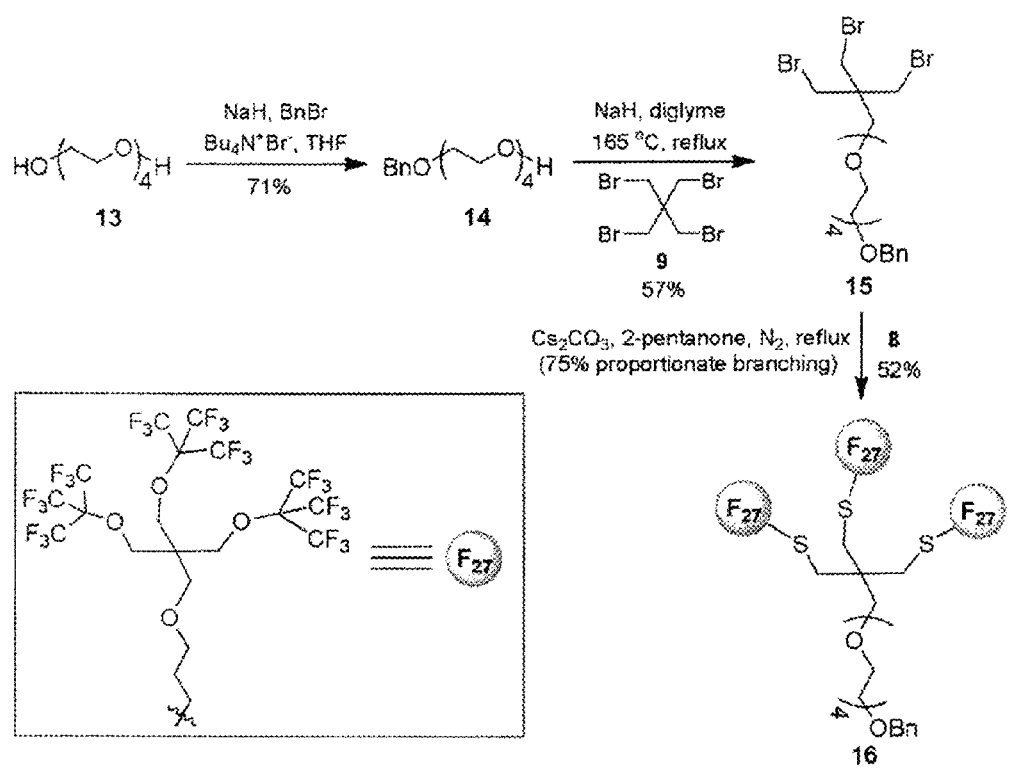
FIG. 7 shows the synthesis of $^{19}$F-81 (Compound 16)$^a$ wherein the 8→16 step is 75% proportional branching.

As shown in FIG. 7, the target $^{19}$F-81 compound 16 was successfully obtained from using tetraethylene glycol compound 13. The $l_2$ in compound 16, which lies between [3×2.5−1, 3×2.5+1], was chosen to be 8. This again is due to a combination of starting material availability and synthesis convenience.

Figure 8A:
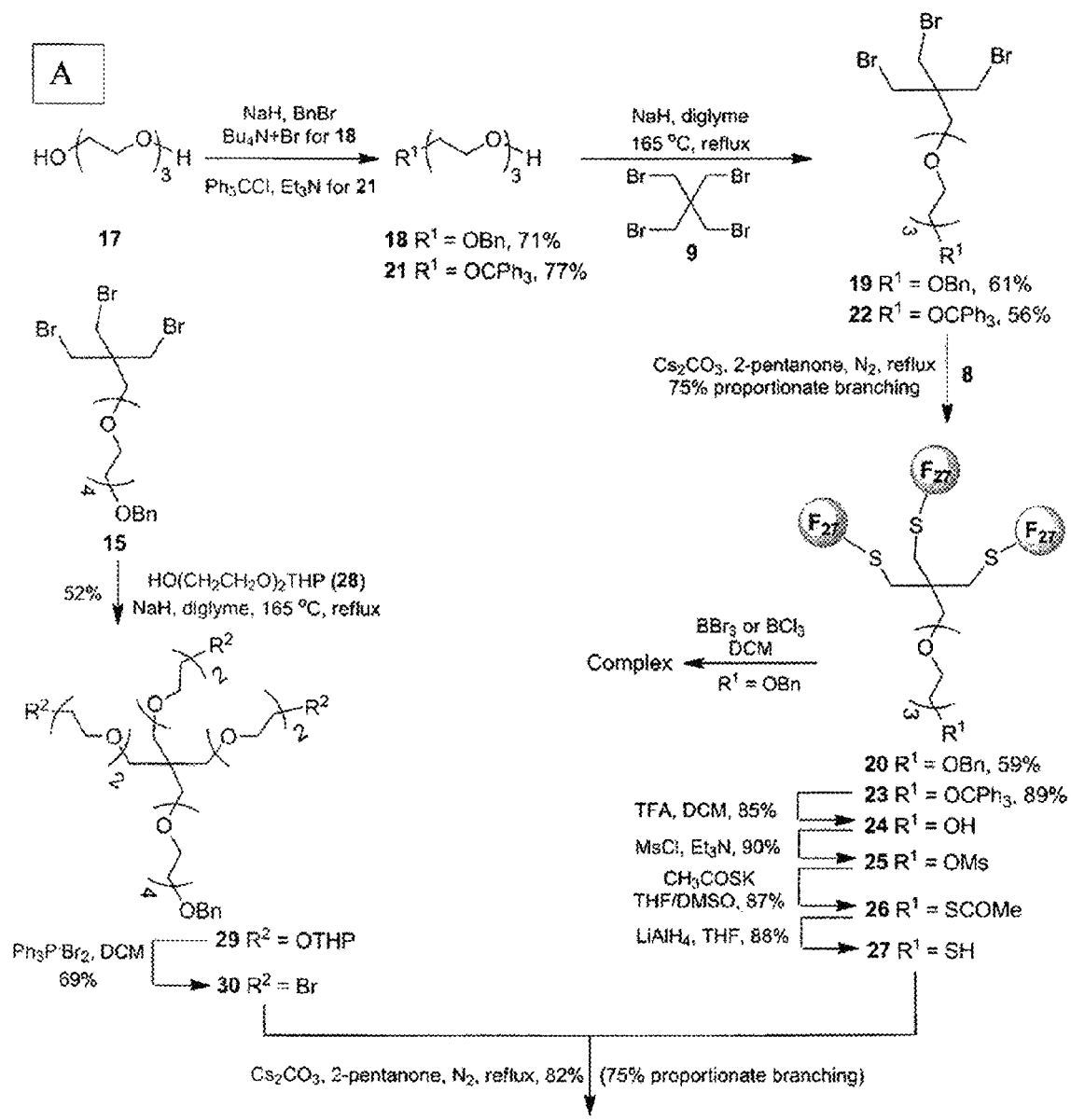
FIGS. 8 A and B show the synthesis of $^{19}$F-243 (Compound 31)$^a$ wherein the 8→20 (or 23) and 27→31 steps are 75% proportionate branching.
Figure 8B:
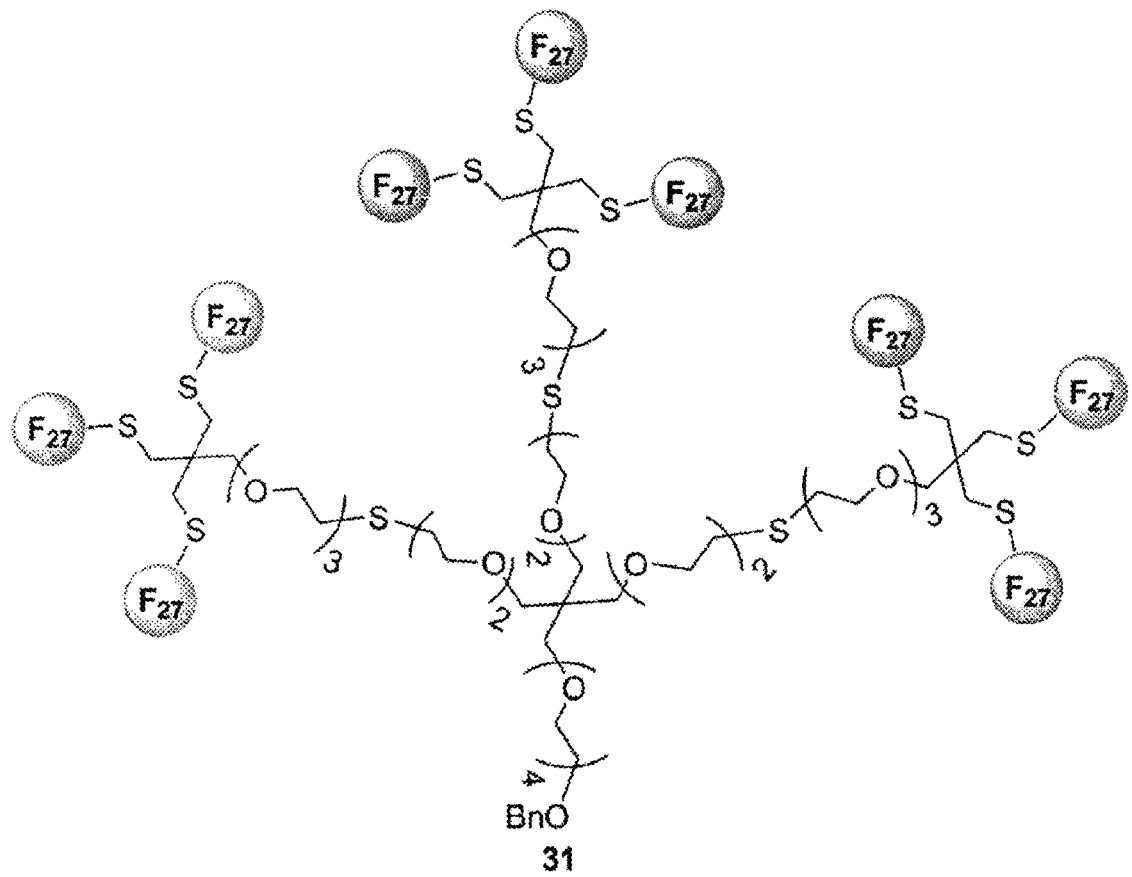

As shown in FIGS. 8A and B, synthesis of $^{19}$F-243 was similar to that of $^{19}$F-81 in that pentaerythritol was used as the branching unit and grafting $^{19}$F-81 onto pentaerythritol utilized the sulfide bond. To satisfy $l_1$=19, the tetraoxyethylene tail in compound 16 was shortened to the trioxyethylene tail in compound 20. However, direct growth from compound 20 to $^{19}$F-243 was hindered by unexpected difficulty in removing the benzyl group in the trioxyethylene tail of $^{19}$F-81. To overcome this difficulty, the benzyl group in compound 18 was replaced by the trityl group in compound 21, which was converted to compound 23. The trityl group in compound 23 was easily removed by TFA to expose a free hydroxyl. Subsequent transformation of this hydroxyl group in compound 24 to the sulfhydryl group in compound 27 proceeded smoothly. Three copies of compound 27 were grafted onto the tribromide compound 30 to give $^{19}$F-243 (compound 31 FIG. 8B) with an 82% yield. In $^{19}$F-243, $l_1$=19, which is at the lower end of [2.5×8−1, 2.5×8+1].

Figure 12:
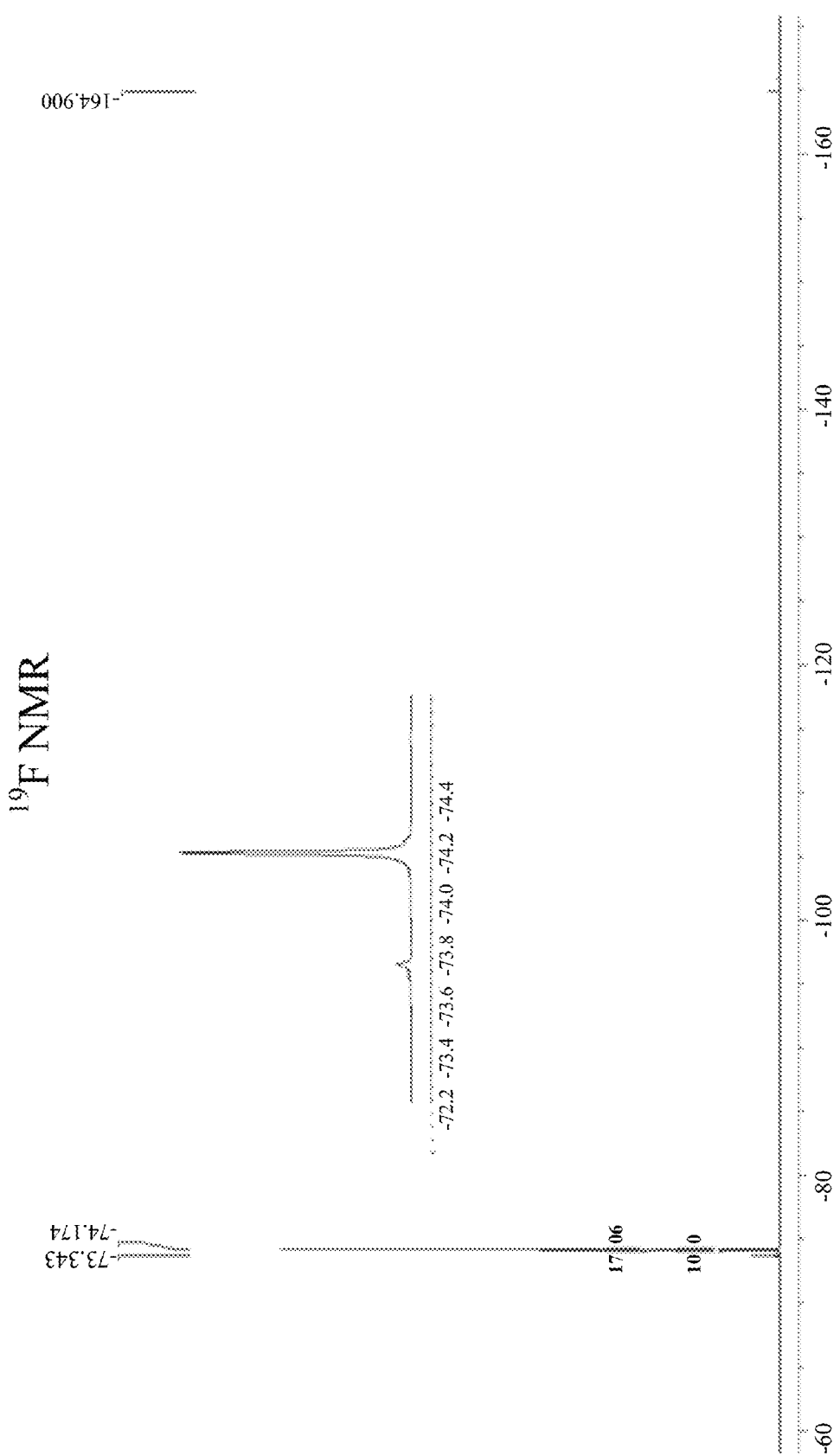
FIG. 12 shows the $^{19}$F NMR spectra for compound 31 and that all four fluorinated dendrons shown in FIGS. 3 and 4 emit a single unsplit sharp $^{19}$F signal.
Figure 12:
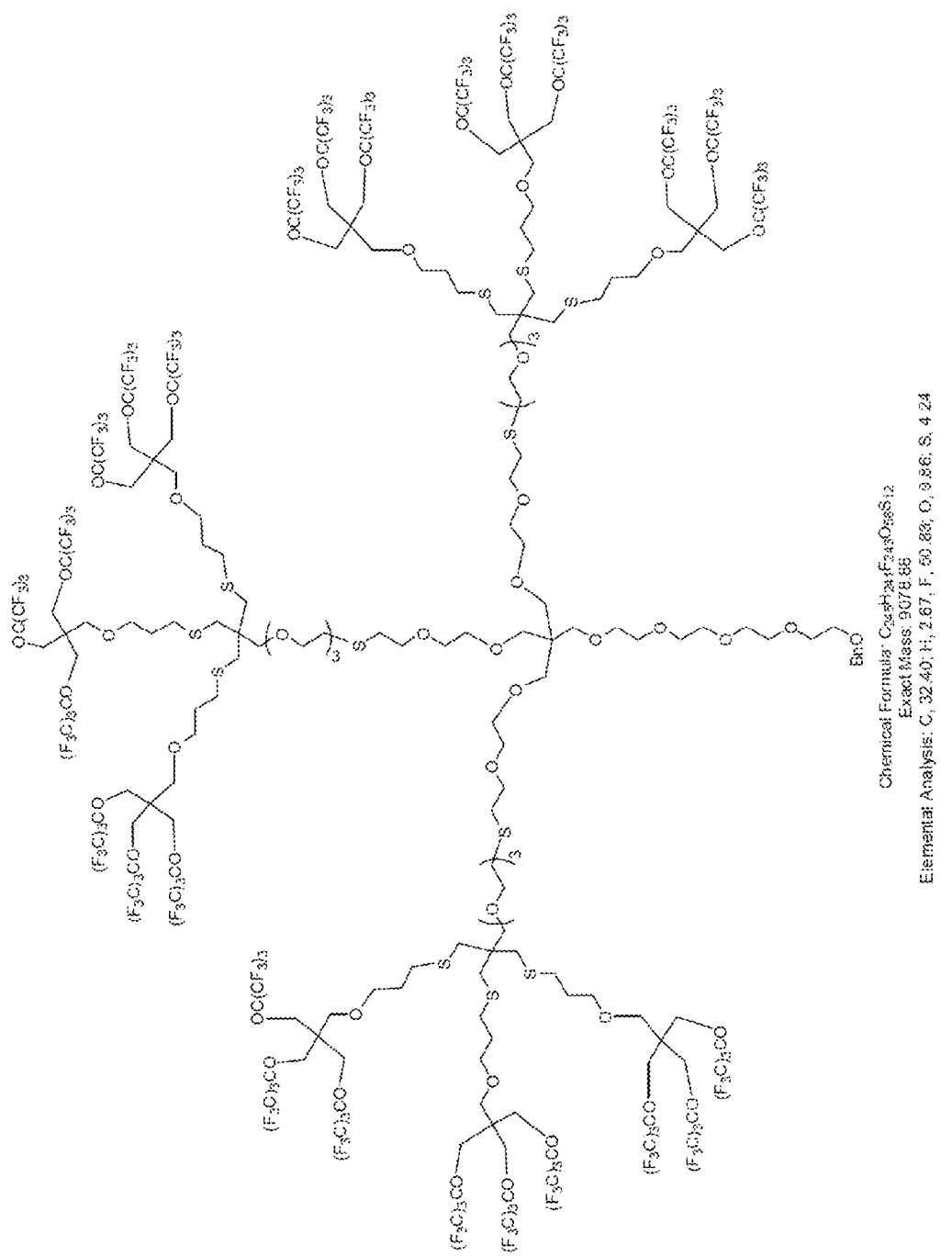

NMR spectroscopy shows that, as expected, all four fluorinated dendrons emit a single unsplit sharp $^{19}$F signal, as shown in FIG. 12, attesting to their potential as imaging agents for $^{19}$F MRI.

Figure 9:
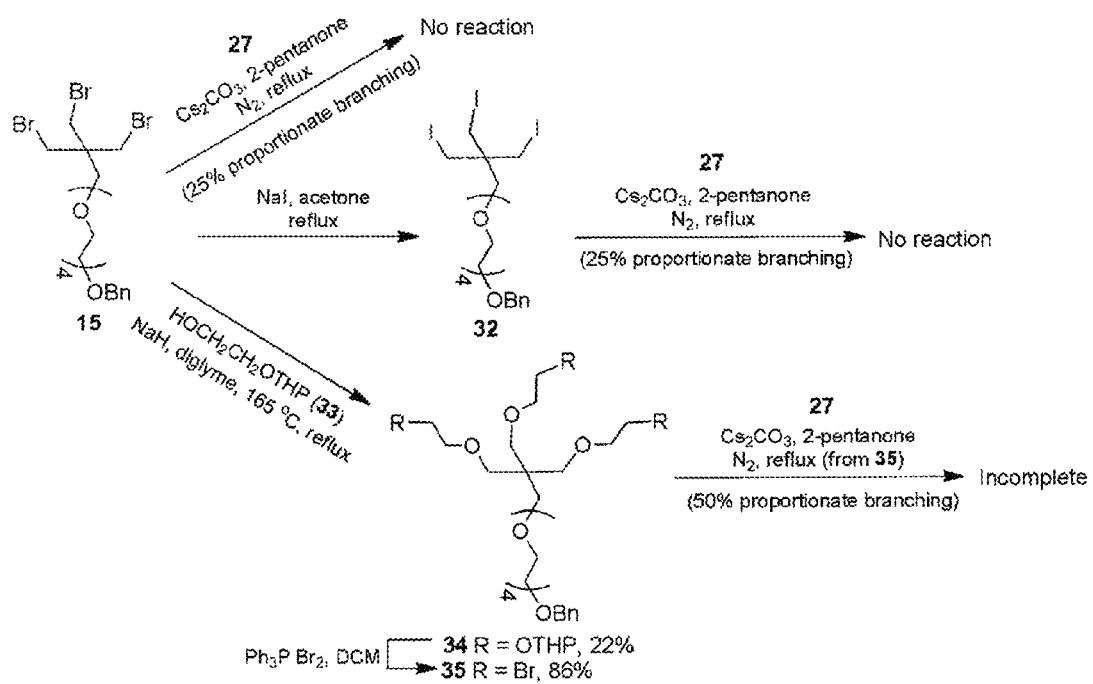
FIG. 9 shows the controlled experiments for growing $^{19}$F-243 with $l_1 = 13$ and 16, which respectively represent 25% and 50% proportionate branching for the $^{19}$F81→$^{19}$F-243 step.

To illustrate the necessity of 75% proportionate branching, control experiments were conducted as shown in FIG. 9. Attempts were made to graft three copies of compound 27 onto compound 15. If successful, this would have led to a $^{19}$F-243 with $l_1$=13, which is equivalent to b=1.5 (13 is in the range of [1.5×8−1, 1.5×8+1]), resulting in c=25%. However, such attempts led to no reaction. Replacing bromide in compound 15 with the more reactive triiodide compound 32 also led to no reaction with compound 27. Then the three bromide side chains in compound 15 were extended by one oxyethylene unit to give another tribromide compound 35. Successful grafting of three copies of compound 27 to compound 35 would have led to a $^{19}$F-243 with $l_1$=16, which is equivalent to b=2 (16 is in the range of [2×8−1, 2×8+1]), resulting in c=50%. However, the reaction was incomplete. This demonstrates that 75% proportionate branching is necessary to avoid steric congestion in the synthesis of these fluorocarbon dendrons.

A previously reported strategy, developed by Xu and Moore in 1993, overcomes steric congestion by growing $l_n$ linearly (i.e., $l_{n-1}$=b+$l_n$), where b is a constant.(24) In contrast, proportionate branching grows $l_n$ exponentially (i.e., $l_{n-1}$=b× $l_n$), where b is a constant. Linear growth of $l_n$ is synthetically simpler, but it has been found herein that exponential growth of $l_n$ can successfully avoid steric congestion in situations where linear growth of $l_n$ fails. Indeed, in the synthesis of the fluorocarbon dendrons from $^{19}$F-9 to $^{19}$F-243, linear growth of $l_n$ would have led to $l_3$=3 ($^{19}$F-9→$^{19}$F-27), $l_2$=8 ($^{19}$F-27→$^{19}$F-81), and $l_1$=13 ($^{19}$F-81→$^{19}$F-243). However, it was shown that for the $^{19}$F-81→$^{19}$F-243 step, $l_1$=13 resulted in no growth at all. Hence, for these fluorocarbon dendrons, linear growth of $l_n$ cannot effectively overcome steric congestion. This is hardly surprising because linear growth of $l_n$ was developed for dendrimers with low branch multiplicity (a=2) while exponential growth of $l_n$ has been developed herein for dendrimers with high branch multiplicity, such as (a=3).

Small-Angle X-Ray Scattering (SAXS) Characterization

For SAXS characterizations, the fluorinated dendrons were dissolved in trifluoroethanol (TFE) at a concentration of 276 mM for compound 3 ($^{19}$F-9), 92.1 mM for compound 5 ($^{19}$F-27), 30.7 mM for compound 16 ($^{19}$F-81) and 10.2 mM for compound 31 ($^{19}$F-243). In all samples, the molar concentration of fluorine is 2,488 mM, or 1.8 mol F/kg. The samples were centrifuged into (20 sec at 500 RPM) the cylindrical glass capillaries with a diameter 1.0 mm and 0.01 mm wall thickness. Small-angle X-ray scattering (SAXS) data were collected at 25° C. using the beamline 12ID-B of Advanced Photon Sources (APS). For every measurement, the X-ray beam with size of 0.07 mm×0.20 mm, was adjusted to pass through the centers of the capillaries. The exposure time for all samples was set to 1 sec to avoid detector saturation and radiation damage to the sample. X-ray scattering intensities were obtained using the 2D detector Pilatus 2M.

The 2D scattering images were converted into 1D scattering profiles I(Q) vs Q by means of azimuthal averaging after solid angle correction followed by normalization over the intensity of the transmitted X-ray beam, using the software package at the beamline 12ID-B. I(Q) is the scattering intensity X-rays, and Q is the scattering vector amplitude which is related to the wavelength λ (0.689 Å) and the scattering angle 2θ by $$Q = \frac{4\pi}{\lambda}\sin(\theta) \quad (2)$$

Figure 13:
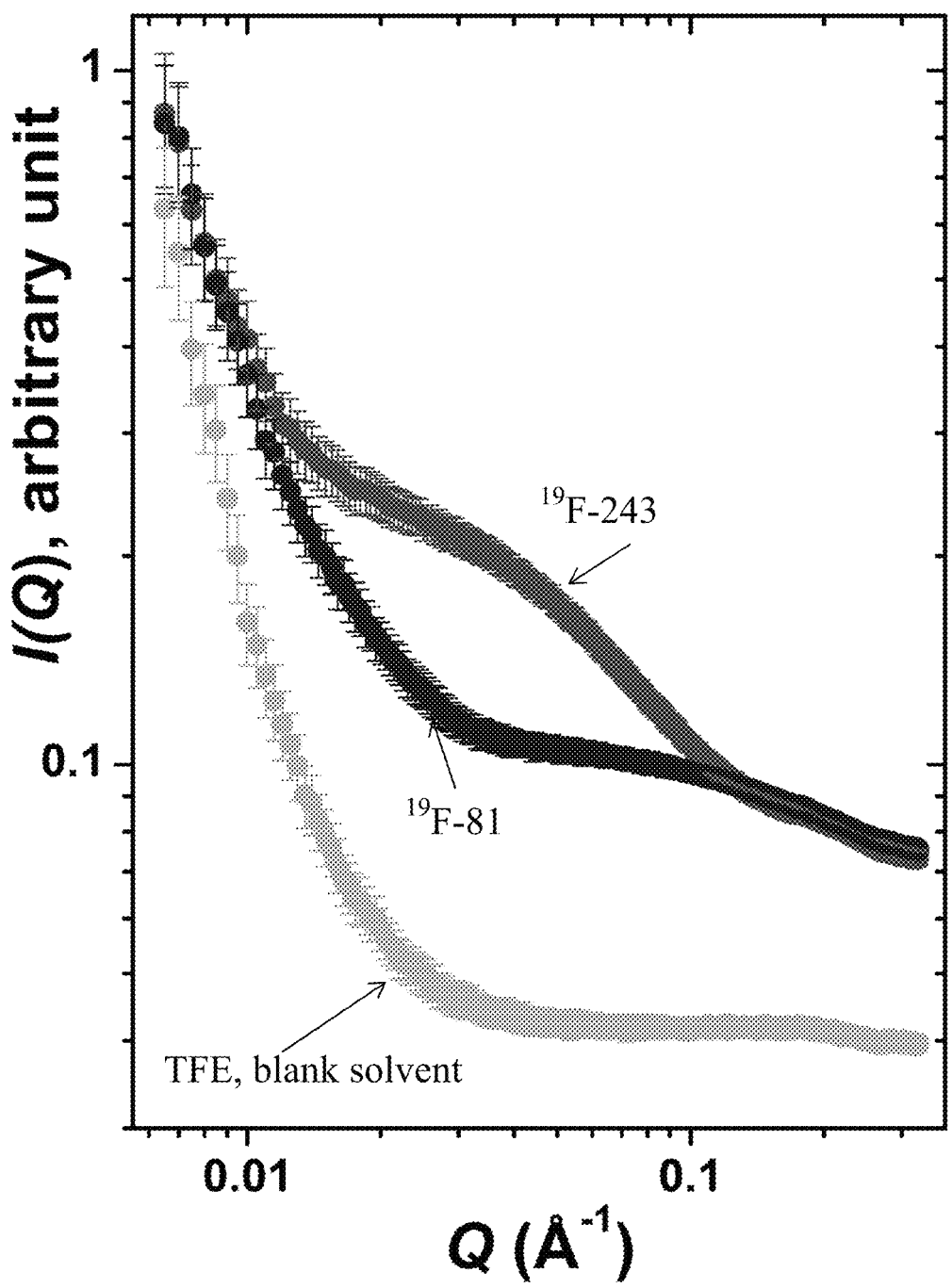
FIG. 13 shows the raw SAXS scattering profiles I(Q) vs. Q before solvent subtraction and background correction. $^{19}$F-81; $^{19}$F-243, TFE blank solvent.
Figure 14B:
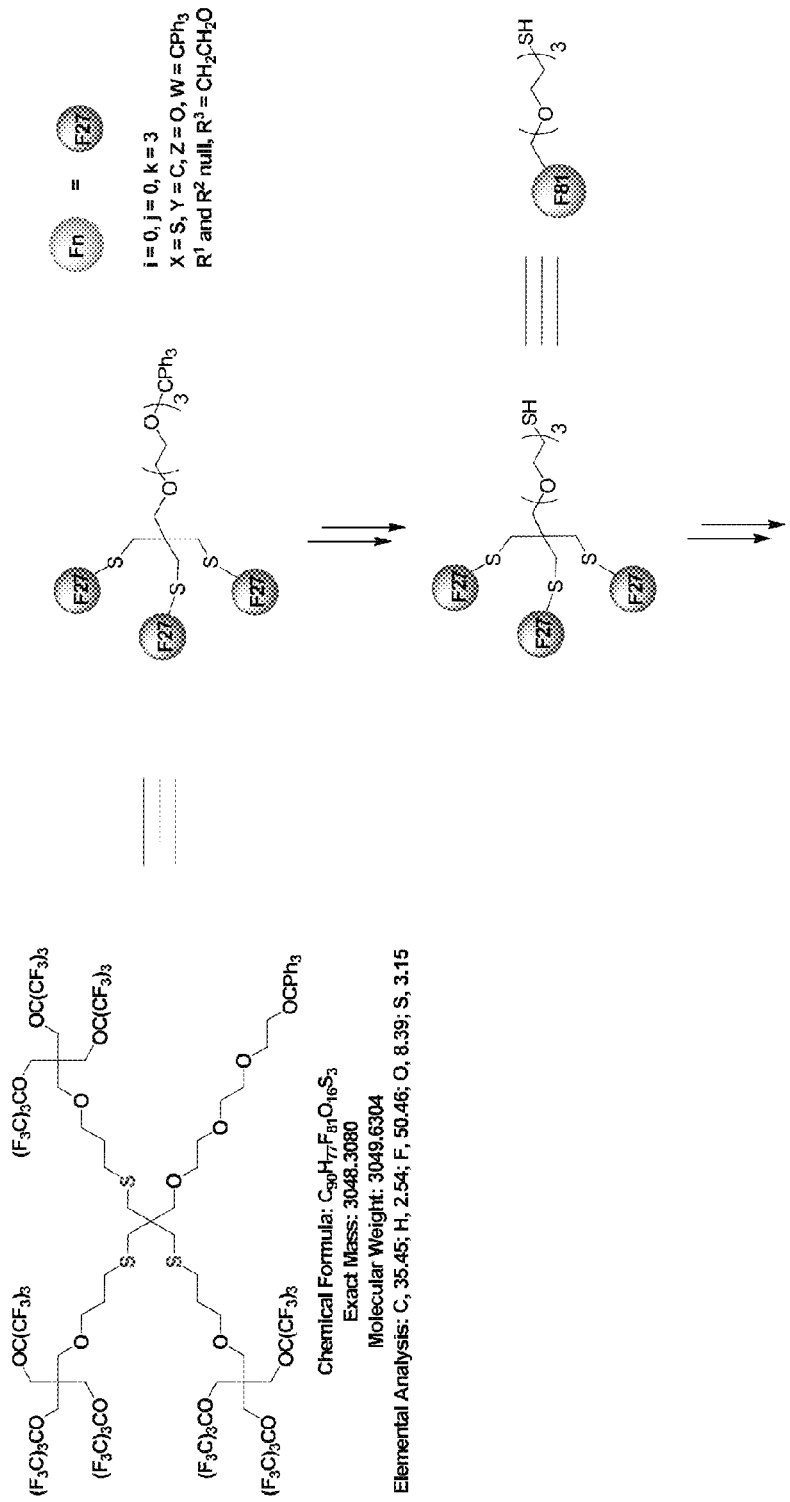
FIGS. 14 A-F show examples of fluorinated Dendron structures that employ proportional branching as described herein.
Figure 14C:
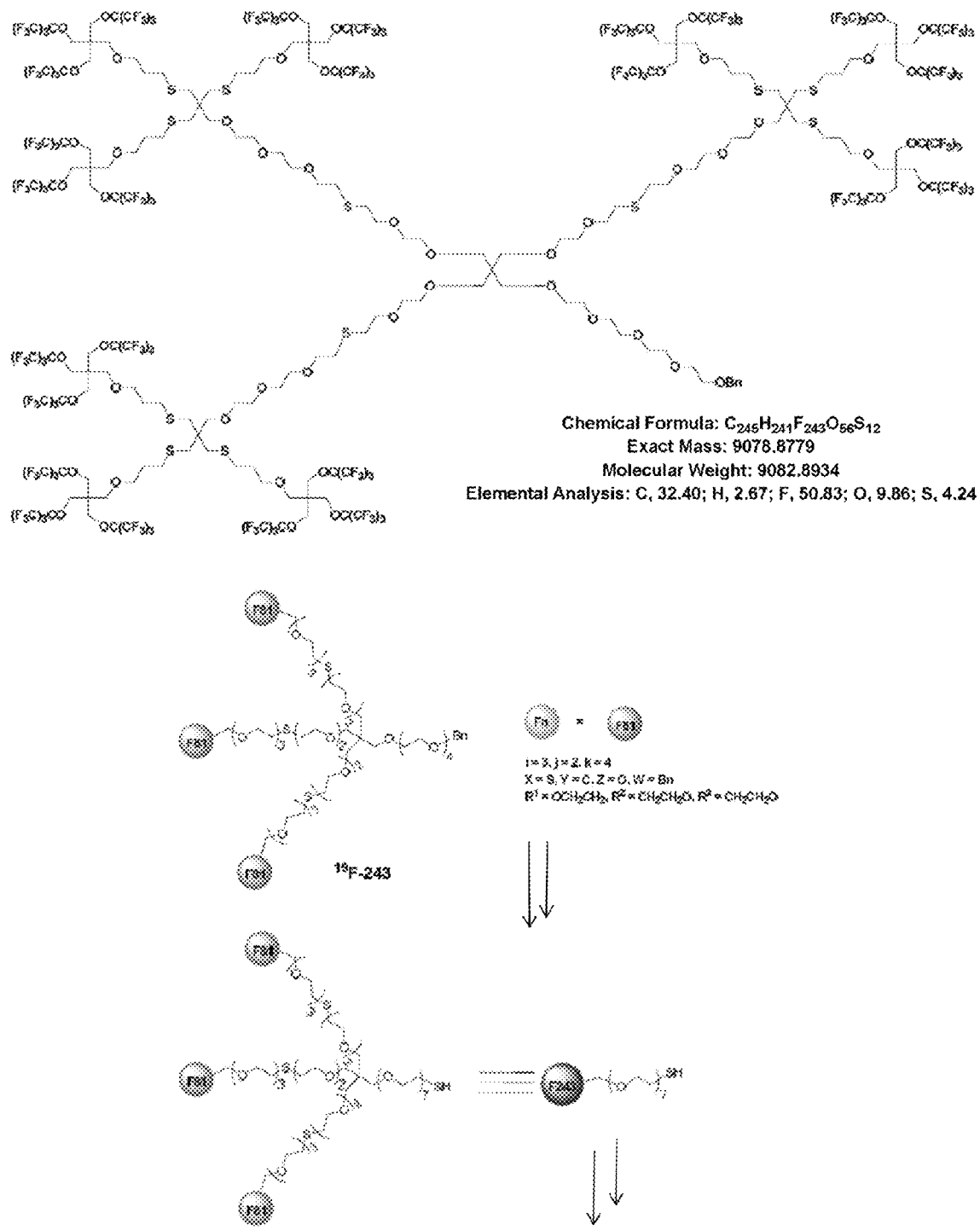
Figure 14:
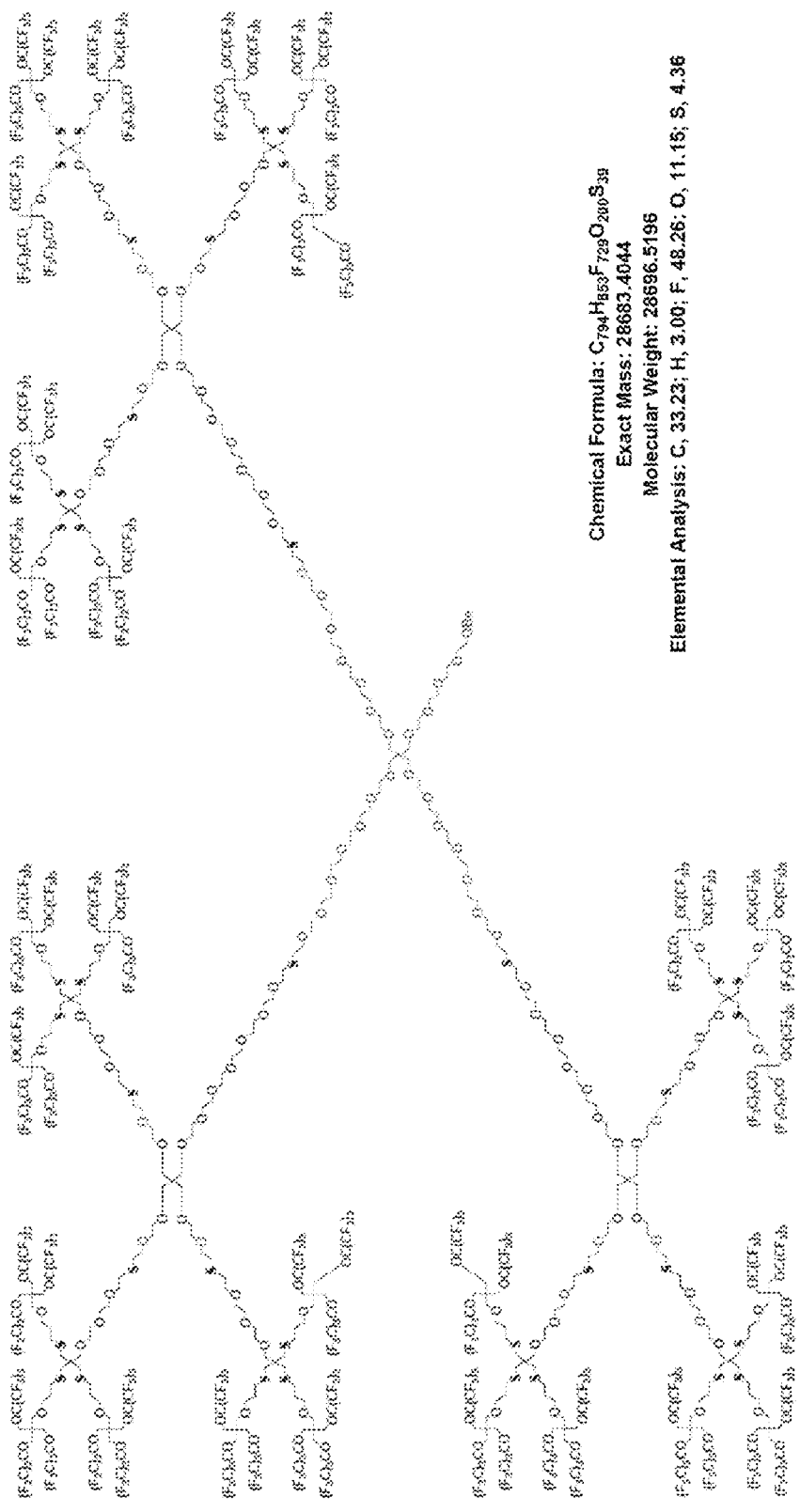
Figure 14F:
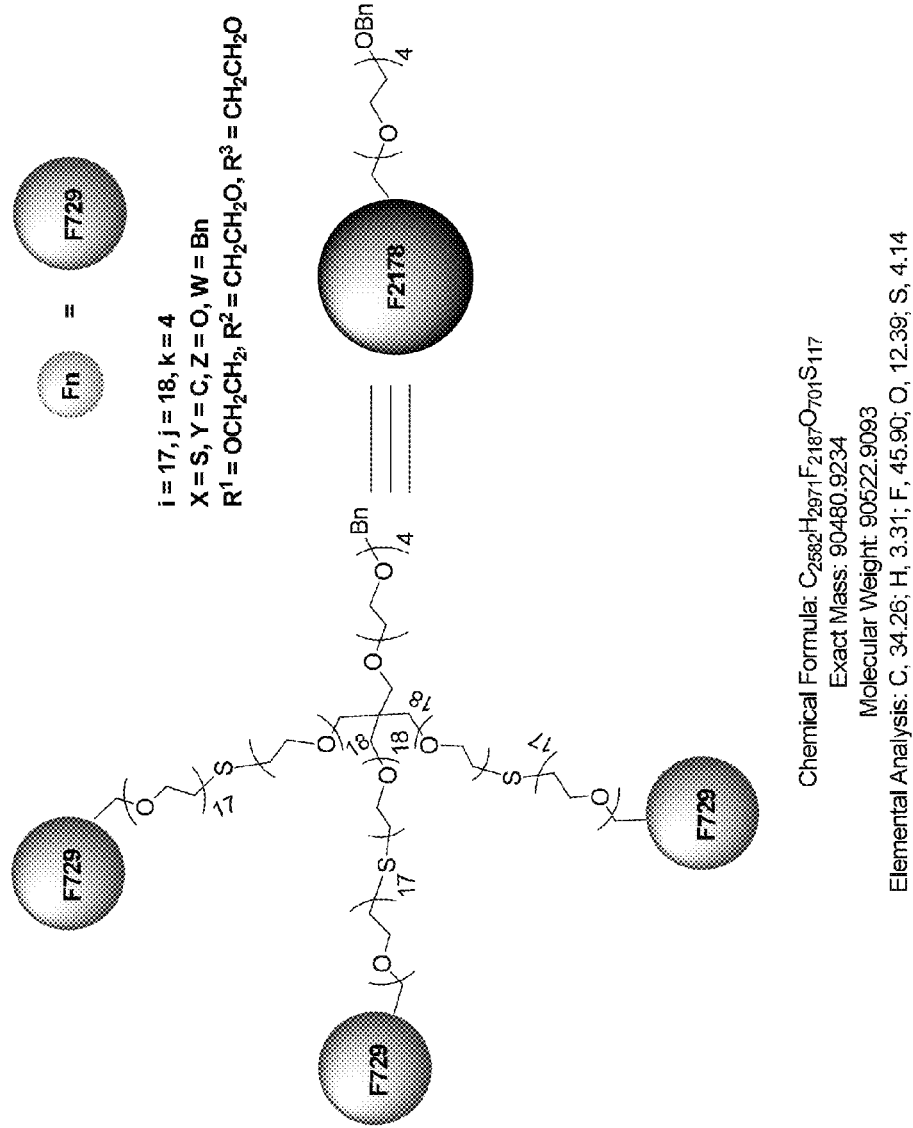

Of the four fluorinated dendrons, only $^{19}$F-81 and $^{19}$F-243 gave sufficient scattering and their structures were characterized by means of ATSAS software.(25, 28) The net scattering from $^{19}$F-243 and $^{19}$F-81 was determined by subtracting the solvent TFE blank scattering profile as shown in FIG. 13. Background scattering correction was performed in accordance with the generally accepted published procedure.(29) The analysis of pair-wise distance distribution functions P(r) (Eq. 3) was performed using linear regularization method in the indirect Fourier-transform techniques in the program GNOM.(25)

$$P(r) = \frac{1}{2\pi^2} \int I(Q) \cdot r \sin(Q \cdot r) dQ \quad (3)$$

P(r) reflects the probability to find different vector lengths connecting two unit-volume elements within the scattering particle, and P(r)=0 at the maximum linear dimension of the particle, $d_{max}$.

The radius of gyration of the scattering particle, $R_g$, is derived from the second moment of P(r) (Eq. 4).

$$R_g^2 = \frac{\int_0^{d_{max}} P(r)r^2 dr}{2\int_0^{d_{max}} P(r) dr} \quad (4)$$

$R_g$ is the root mean square distance of all unit-volume elements from the center of gravity of the scattering particle, and in the case of X-rays, the distribution of the mass is defined by the electron density distribution within the scattering volume.

Simulated annealing algorithm was used to restore low resolution 3D structures of $^{19}$F-81 and $^{19}$F-243 in solution built from densely packed dummy atom models implemented in the DAMMIF program.(30) To build the most probable and reliable 3D model, multiple DAMMIF solutions (at least 20 runs for each $^{19}$F-81 and $^{19}$F-243) were aligned and averaged using DAMAVER routine.(31)

Figure 10:
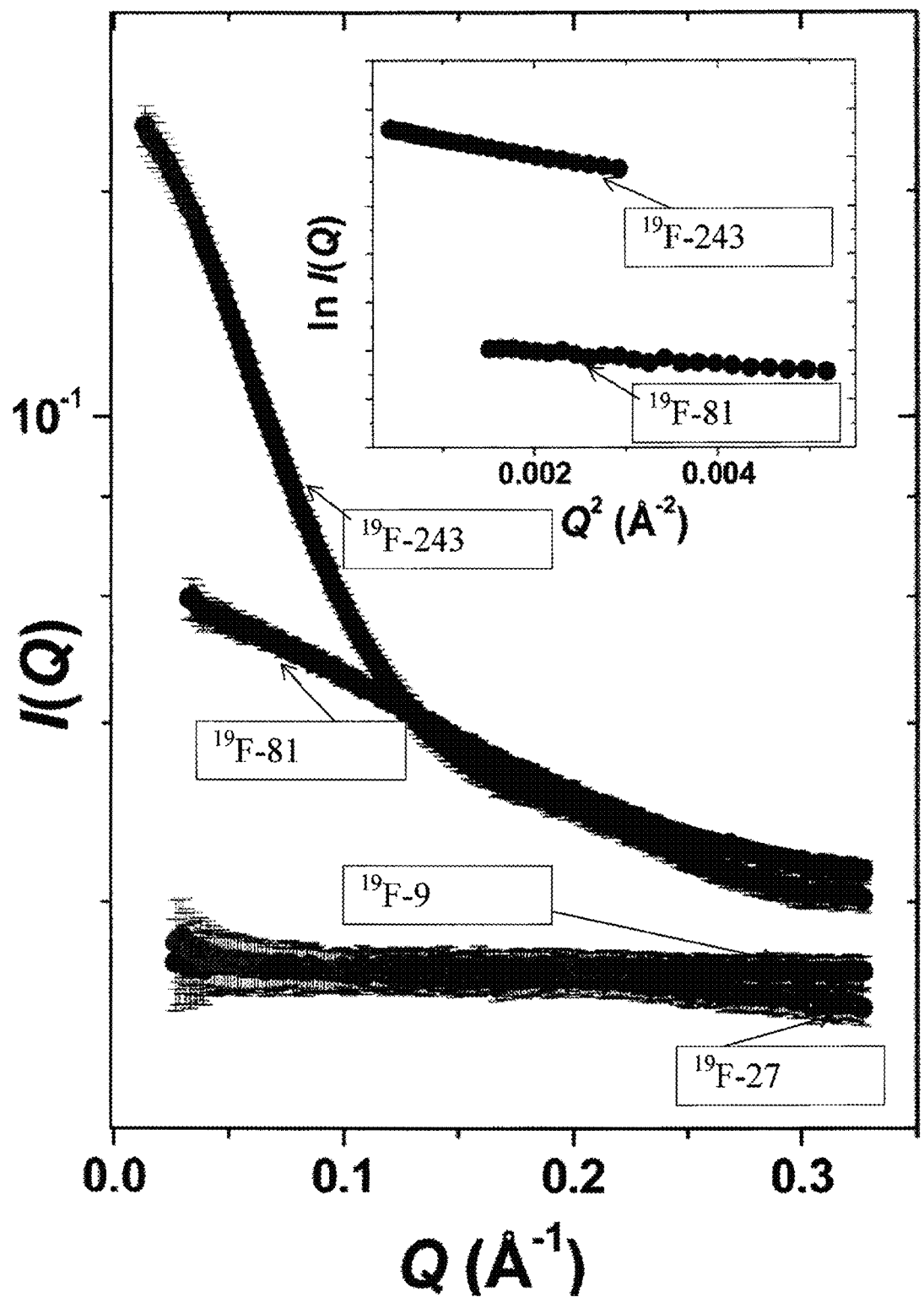
FIG. 10 shows the I(Q) vs Q SAXS profiles of $^{19}$F-243 and $^{19}$F-81 after solvent subtraction and background correction; the scattering profiles of $^{19}$F-27 and $^{19}$F-9 are shown for comparison. Inset plot shows the linear region of Guinier plot of lnI(Q) vs $Q^2$ for globular particles, for the Q range where $QR_g < 1.3$ (Q range ~0.039-0.072 Å$^{-1}$ for $^{19}$F-81 and ~0.021-0.054 Å$^{-1}$ for $^{19}$F-243). Statistical error bars correspond to one standard deviation and represent error in scattering intensity estimation.

SAXS profiles of I(Q) versus Q of the four compounds are shown in FIG. 10, where I(Q) is the scattering intensity and Q is the amplitude of the scattering vector and is equal to (4π/λ)sin(θ/2), where θ is the scattering angle and λ is the wavelength of the incident X-ray (0.689 Å). Of these four compounds, only $^{19}$F-81 (MW=2941 Da) and $^{19}$F-243 (MW=9082 Da) are large enough to give sufficient scattering intensity at the aforementioned concentrations. $^{19}$F-243 gave much stronger X-ray scattering than $^{19}$F-81 in the lower Q region, indicative of much larger scattering particles.

The linearity in the Guinier plot (FIG. 10, inset) suggests monodispersity for both $^{19}$F-81 and $^{19}$F-243 in TFE solution, as shown in FIGS. 11A and B. Indeed, indirect Fourier transform of the scattering profiles results in pairwise distance distribution P(r) functions with good quality (fitting quality of the P(r) functions was ~0.7-0.8, which indicates good fit; for an ideal fit, the criterion is $1.0^{25}$). In the case of $^{19}$F-81, the P(r) profile describes an elongated slightly asymmetrical object (FIG. 11 C). In the case of $^{19}$F-243, the P(r) profile has two pronounced maxima and is characteristic for distinct dumbbell shaped particles (FIG. 11D). From the r value at which P(r)=0, the maximum linear dimension of each particle, $d_{max}$, could be estimated, which is 55 Å for $^{19}$F-81 and 85 Å for $^{19}$F-243. For each dendron, the maximum distance between the fluorine atoms in the head and the benzyl group in the tail can be estimated by multiplying the number of bonds between them, which is 28 for $^{19}$F-81 and 47 for $^{19}$F-243, and the average bond length, which is ~1.7 Å. The resulting values are ~50 Å for $^{19}$F-81 and ~80 Å for $^{19}$F-243, which are in good agreement with $d_{max}$ obtained from SAXS measurement. Such agreement suggests $^{19}$F-81 and $^{19}$F-243 exist as monomers in TEF, attesting that TFE (F %=57%), even though relatively polar with a dielectric constant of 28, is a good solvent for $^{19}$F-81 (F %=52%) and $^{19}$F-243 (F %=51%). The values of the radius of gyration, $R_g$, derived from the above P(r) functions are 17.9 and 24.8 Å for $^{19}$F-81 and $^{19}$F-243, respectively. For both $^{19}$F-81 and $^{19}$F-243, $R_g$ is markedly smaller than $d_{max}/2$ (22.5 and 42.5 Å, respectively, for $^{19}$F-81 and $^{19}$F-243). This indicates that the center of the scattering electron "mass" in both molecules is moved toward the electron-rich fluorocarbon head of each molecule, as one would expect.

To restore low-resolution 3D shapes of $^{19}$F-81 and $^{19}$F-243, the ab initio program DAMMIN was used.(26) More than 20 possible structures generated by DAMMIN for each $^{19}$F-81 and $^{19}$F-243 were superimposed using the best-matching alignment program SUPCOMB.(27) The normalized structural discrepancy parameter (NSD), which characterizes structural similarity of DAMMIN results, was ~0.3 for both substances (NSD=0 for ideal similarity, and NSD>1 for systemically different structures). The restored low-resolution 3D shapes of $^{19}$F-81 and $^{19}$F-243 in TFE solution are both dumbbells (FIG. 11C,D), though much less pronounced in the case of $^{19}$F-81. Such dumbbell shape is consistent with the chemical structures of $^{19}$F-81 and $^{19}$F-243, with the larger lobe being the fluorocarbon head and the smaller lobe being the oxyethylene tail. The spherical symmetry of the fluorocarbon head of each molecule is consistent with complete dendrimer growth for both $^{19}$F-81 and $^{19}$F-243.

From the chemical structures of $^{19}$F-81 and $^{19}$F-243, one might expect much greater differences between the dimensions of the fluorocarbon head and the oxyethylene tail. However, what SAXS measures is not the geometric volume, but the averaged scattering volume, which is influenced by molecular compactness and flexibility in solution. The apolar fluorocarbon chains are likely to cluster in the relatively polar TFE, leading to smaller than expected scattering volume. The polar oxyethylene tail, (—OCH$_2$CH$_2$—)$_4$—OBn, is likely to be flexible in TFE, leading to larger than expected scattering volume.

Proportionate branching is proposed to avoid steric congestion in dendrimer growth. The effectiveness of this strategy is demonstrated through the synthesis of four generations of fluorinated dendrons, containing up to 243 chemically identical fluorine atoms per dendron. The SAXS investigation indicates that generations 3 and 4 dendrons both have a dumbbell shape with spherical symmetry for the fluorine part, as designed. Proportionate branching will be particularly useful in making dendrimers with high branch multiplicity and bulky periphery groups. Emulating the structure of living organisms might be a general strategy for making defect-free functional macromolecules. The key is to translate biological observations into principles amenable to chemical synthesis.

Spectra Methods

Unless otherwise stated, all chemicals were obtained from commercial sources and used without further purification. Analytical thin layer chromatography (TLC) was performed on precoated silica gel 60 F254 plates with visualization by ultraviolet (UV) irradiation at λ=254 nm or staining with KMnO$_4$. Purifications were performed by silica gel chromatography. The $^1$H, $^{19}$F, and $^{13}$C NMR spectra were carried out on a 500 MHz spectrometer. The $^1$H, $^{19}$F, and $^{13}$C NMR spectra were recorded at 500, 470, and 126 MHz, respectively. $^1$H NMR chemical shifts (δ) are reported in parts per million (ppm) relative to a residual proton peak of the solvent, δ=7.24 for CDCl$_3$, δ=2.80 for CD$_3$COCD$_3$. Multiplicities are reported as follows: s (singlet), d (doublet), t (triplet), q (quartet), dd (doublet of doublets), or m (multiplet). Broad peaks are indicated by the addition of br. Coupling constants are reported as a J value in hertz (Hz). The number of protons (n) for a given resonance is indicated as nH and is based on spectral integration values. $^{13}$C NMR chemical shifts (δ) are reported in ppm relative to CDCl$_3$ (δ=77.3) or CD$_3$COCD$_3$ (δ=206.8). For $^{19}$F NMR, hexafluorobenzene was used as the internal standard at δ −164.9 ppm. Molecular mass was performed on either MALDI-TOF or on an ion trap mass spectrometer using the DirectProbe add-on inserted into the atmospheric pressure chemical ionization (APCI) housing. HRMS data were collected using AccuTOF. For compounds containing 81 and 243 fluorine atoms, HRMS data could not be obtained in spite of repeated tries. However, their LRMS data obtained using a DirectProbe showed the correct mass.

tert-Butyl 3-(3-hydroxy-2,2-bis(hydroxymethyl)propoxy)propanoate (2)

To DMSO (100 mL) was added pentaerythritol 1 (68 g, 0.5 mol); the heterogeneous suspension was heated to 80° C. until the system became clear, then aqueous NaOH (4 g of NaOH in 9 mL of H$_2$O) was added in one portion, tert-butyl acrylate (87 mL, 0.6 mol) was added to the solution dropwise, and vigorous stirring continued overnight at 80° C. After cooling, the solution was extracted with EtOAc. The combined organic phase was washed with H$_2$O and brine, concentrated through rotary evaporation, and the residue was subjected to silica gel chromatography using CH$_2$Cl$_2$/MeOH as the eluent to give 2 (54.3 g, 0.21 mol, 41% yield) as a clear oil: $^1$H NMR (500 MHz, CDCl$_3$) δ 3.63 (br, 3H), 3.56 (t, J=5.5 Hz, 2H), 3.52 (s, 6H), 3.37 (s, 2H), 2.38 (t, J=5.0 Hz, 2H), 1.37 (s, 9H); $^{13}$C NMR (126 MHz, CDCl$_3$) δ 171.7, 81.2, 72.1, 67.2, 63.6, 45.3, 36.1, 28.1; MS (ESI) m/z 209 (M−$^t$Bu+2H)$^+$, 265 (M+H)$^+$, 287 (M+Na)$^+$; HRMS (ESI) calcd for C$_{12}$H$_{25}$O$_6$ 265.1651 (M+H)$^+$, 209.1025 [M−$^t$Bu+2H]$^+$. found 265.1646, 209.1026, respectively.

tert-Butyl 3-(3-((1,1,1,3,3,3-hexafluoro-2-(trifluoromethyl)propan-2-yl)oxy)-2,2-bis(((1,1,1,3,3,3-hexa-fluoro-2-(trifluoromethyl)propan-2-yl)oxy)methyl)propoxy)propanoate (4)

To a stirred suspension of compound 2 (26.4 g, 100 mmol), triphenylphosphine (118 g, 450 mmol), and 4 Å molecular sieves (15 g) in tetrahydrofuran (700 mL) at 0° C. was added dropwise diisopropylazodicarboxylate (90 mL, 450 mmol). Afterward, the reaction mixture was allowed to warm to room temperature and was stirred for an additional 20 min. Then perfluoro-tert-butanol 3 (62.5 mL, 450 mmol) was added in one portion, and the resulting mixture was stirred for 36 h at 45° C. in a sealed vessel. Water (30 mL) was added to the reaction mixture and stirred for an additional 10 min. Then the mixture was transferred to a separatory funnel, and the lower phase was collected. Removal of the perfluoro-tert-butanol under vacuum gave the product 4 (65 g, 70.8 mmol, 71% yield) as a clear oil: $^1$H NMR (500 MHz, CDCl$_3$) δ 4.08 (s, 6H), 3.66 (t, J=6.0 Hz, 2H), 3.45 (s, 2H), 2.46 (t, J=6.0 Hz, 2H), 1.45 (s, 9H); $^{13}$C NMR (126 MHz, CDCl$_3$) δ 170.6, 120.4 (q, J=293.3 Hz), 80.8, 80.4-79.2 (m), 67.4, 66.6, 66.1, 46.4, 36.0, 28.0; $^{19}$F NMR (470 MHz, CDCl$_3$) δ −73.50 (s); MS (APCI) m/z 863 (M−$^t$Bu+2H)$^+$, 791 (M−$^t$BuOCOCH$_2$CH$_2$+2H)$^+$; HRMS (ESI) calcd for C$_{24}$H$_{25}$F$_{27}$NO$_6$ 936.1251 (M+NH$_4$)$^+$, 863.0359 [M−$^t$Bu+2H]$^+$. found 936.1232, 863.0294, respectively.

3-(3-((1,1,1,3,3,3-Hexafluoro-2-(trifluoromethyl)propan-2-yl)oxy)-2,2-bis(((1,1,1,3,3,3-hexafluoro-2-(trifluoromethyl)propan-2-yl)oxy)methyl) propoxy)propan-1-ol (5)

(—OH version of $^{19}$F-27): To a suspension of lithium aluminum hydride (4.1 g, 108 mmol) in THF solution (450 mL) at 0° C. was added dropwise compound 4 (40 g, 43.5 mmol) in THF (100 mL). Afterward, the solution was stirred overnight at room temperature and quenched with dilute HCl carefully, concentrated through rotary evaporation, and subjected to silica gel chromatography using hexane/EtOAc as the eluent to afford alcohol 5 (33.7 g, 39.7 mmol, 91% yield) as a clear oil: $^1$H NMR (500 MHz, CDCl$_3$) δ 4.02 (s, 6H), 3.69 (t, J=6.0 Hz, 2H), 3.51 (t, J=4.5 Hz, 2H), 3.37 (s, 2H), 1.82-1.77 (m, 2H), 1.47 (s, 9H); $^{13}$C NMR (126 MHz, CDCl$_3$) δ 120.4 (q, J=294.7 Hz), 80.1-79.4 (m), 69.3, 66.3, 66.7, 60.4, 46.4, 32.5; $^{19}$F NMR (470 MHz, CDCl$_3$) δ—73.40 (s); MS (APCI) m/z 849 (M+H)$^+$; HRMS (ESI) calcd for C$_{20}$H$_{16}$F$_{27}$O$_5$ 849.0567 (M+H)$^+$, 866.0832 [M+NH$_4$]+. found 849.0577, 866.0811, respectively.

3-(3-((1,1,1,3,3,3-Hexafluoro-2-(trifluoromethyl)propan-2-yl)oxy)-2,2-bis(((1,1,1,3,3,3-hexafluoro-2-(trifluoromethyl)propan-2-yl)oxy)methyl)propoxy)propyl methanesulfonate (6)

Triethylamine (Et$_3$N, 9.6 mL) and methanesulfonyl chloride (5.4 mL, 68.4 mmol) were added to a solution of compound 5 (20.2 g, 23.8 mmol) dissolved in THF (100 mL) and anhydrous CH$_2$Cl$_2$ (200 mL) mixed solvent at 0° C. The reaction mixture was then stirred at room temperature overnight. The reaction was quenched with water and extracted with CH$_2$Cl$_2$. Evaporation through rotary evaporation followed by flash chromatography on silica gel using hexane/EtOAc as the eluent afforded product mesylate 6 (20.8 g, 22.5 mmol, 95% yield) as a colorless oil: $^1$H NMR (500 MHz, CD$_3$COCD$_3$) δ 4.21 (t, J=7.5 Hz, 2H), 4.11 (s, 6H), 3.48 (t, J=5.0 Hz, 2H), 3.42 (s, 2H), 2.94 (s, 3H), 1.94-1.90 (m, 2H); $^{13}$C NMR (126 MHz, CD$_3$COCD$_3$) δ 122.9 (q, J=293.0 Hz), 81.2-81.0 (m), 68.6, 68.5, 67.1, 67.0, 47.7, 37.6, 30.7; $^{19}$F NMR (470 MHz, CD$_3$COCD$_3$) δ −71.19 (s); MS (APCI) m/z 927 (M+H)$^+$, 831 (M−OMs)+; HRMS (ESI) calcd for C$_{21}$H$_{18}$F$_{27}$O$_7$S, 927.0342 (M+H)$^+$, 944.0608 [M+NH$_4$]+. found 927.0357, 944.0553, respectively.

(S)-(3-(3-((1,1,1,3,3,3-Hexafluoro-2-(trifluoromethyl)propan-2-yl)oxy)-2,2-bis(((1,1,1,3,3,3-hexafluoro-2-(trifluoromethyl)propan-2-yl)oxy)methyl)propoxy) propyl)ethanethioate (7)

To a solution of mesylate 6 (10.2 g, 11 mmol) in DMF (100 mL) was added potassium thioacetate (3.8 g, 33 mmol). The reaction mixture was stirred at 50° C. overnight. The mixture was then extracted with DCM, washed successively with water and brine, concentrated through rotary evaporation, and subjected to silica gel chromatography using hexane/EtOAc as the eluent to afford the thioester 7 (9.3 g, 10.3 mmol, 93% yield) as a light yellow liquid: $^1$H NMR (500 MHz, CDCl$_3$) δ 3.97 (s, 6H), 3.34 (t, J=7.0 Hz, 2H), 3.29 (s, 2H), 2.80 (t, J=6.5 Hz, 2H), 2.21 (s, 3H), 1.73 (t, J=7.0 Hz, 2H); $^{13}$C NMR (126 MHz, CDCl$_3$) δ 195.7, 120.4 (q, J=293.2 Hz), 80.2-79.5 (m), 70.2, 66.2, 65.8, 46.5, 30.5, 29.7, 26.0; $^{19}$F NMR (470 MHz, CDCl$_3$) δ −73.25 (s); MS (APCI) m/z 907 (M+H)$^+$; HRMS (ESI) calcd for C$_{22}$H$_{18}$F$_{27}$O$_5$S, 907.0444 (M+H)$^+$, 924.0709 [M+NH$_4$]$^+$. found 907.0430, 924.0782, respectively.

3-(3-((1,1,1,3,3,3-Hexafluoro-2-(trifluoromethyl)propan-2-yl)oxy)-2,2-bis(((1,1,1,3,3,3-hexafluoro-2-(trifluoromethyl)propan-2-yl)oxy)methyl) propoxy) propane-1-thiol (8)

(—SH version of $^{19}$F-27): At 0° C., to a solution of thioester 7 (8.6 g, 9.5 mmol) in THF (90 mL) was added lithium aluminum hydride (0.90, 23.8 mmol) in one portion under nitrogen. After the starting material was consumed completely as monitored by TLC, the reaction was quenched with dilute HCl carefully under nitrogen, concentrated through rotary evaporation, and subjected to silica gel chromatography using hexane/EtOAc as the eluent to give compound 8 (8.0 g, 9.3 mmol, 98% yield) as a clear oil: $^1$H NMR (500 MHz, CDCl$_3$) δ 4.02 (s, 6H), 3.46 (t, J=7.5 Hz, 2H), 3.36 (s, 2H), 2.53 (dd, J=7.5, 16.0 Hz, 2H), 1.85-1.80 (m, 2H), 1.29 (t, J=8.0 Hz, 1H); $^{13}$C NMR (126 MHz, CDCl$_3$) δ 120.4 (q, J=293.5 Hz), 79.9-79.4 (m), 69.8, 66.1, 66.6, 46.5, 33.9, 14.0; $^{19}$F NMR (470 MHz, CDCl$_3$) δ −73.51 (s); MS (APCI) m/z 865 (M+H)$^+$, 791 (M−HSCH$_2$CH$_2$CH$_2$+2H)$^+$; HRMS (ESI) calcd for C$_{20}$H$_{16}$F$_{27}$O$_4$S, 865.0338 (M+H)$^+$, 882.0624 [M+NH$_4$]$^+$. found 865.0306, 882.0582, respectively.

(2-(3-Bromo-2,2-bis(bromomethyl)propoxy)ethoxy)methyl)benzene (11

To a suspension of sodium hydride (0.4 g, 10 mmol, 60% dispersion in mineral oil) in 40 mL of DMF at 0° C. was added a solution of monoprotected ethylene glycol 10 (1.0 g, 6.6 mmol) dropwise. The resulting mixture was stirred at 0° C. for 0.5 h and then at room temperature for another 1 h to give the solution of sodium alcoholate. Pentaerythritol tetrabromide 9 (2.9 g, 7.6 mmol) was added. Afterward, the mixture was heated at 60° C. for 24 h and then cooled to room temperature. The reaction mixture was quenched with H$_2$O and extracted with EtOAc, concentrated through rotary evaporation and subjected to silica gel chromatography using hexane/EtOAc as the eluent to give compound 11 (1.18 g, 2.6 mmol, 39% yield) as a light yellow liquid: $^1$H NMR (500 MHz, CDCl$_3$) δ 7.34-7.33 (m, 4H), 7.29-7.27 (m, 1H), 4.55 (s, 2H), 3.64 (dd, J=4.5 Hz, 19.0 Hz, 4H), 3.55 (s, 2H), 3.53 (s, 6H); $^{13}$C NMR (126 MHz, CDCl$_3$) δ 138.4, 128.6, 127.88, 127.85, 73.4, 71.3, 70.1, 69.6, 44.0, 35.1; MS (ESI) m/z 458 (M+H)$^+$, 474 (M+NH$_4$)$^+$; HRMS (ESI) calcd for C$_{14}$H$_{23}$Br$_3$NO$_2$ 475.9258 (M+NH$_4$)$^+$. found 475.9236.

13-((2-(Benzyloxy)ethoxy)methyl)-1,1,1,25,25,25-hexafluoro-13-(((3-(3-((1,1,1,3,3,3-hexafluoro-2-(trifluoromethyl)propan-2-yl)oxy)-2,2-bis(((1,1,1,3,3,3-hexafluoro-2-(trifluoromethyl)propan-2-yl)oxy)methyl)propoxy)propyl)thio)methyl)-5,5,21,21-tetrakis(((1,1,1,3,3,3-hexafluoro-2-(trifluoromethyl)propan-2-yl)oxy)methyl)-2,2,24,24-tetrakis(trifluoromethyl)-3,7,19,23-tetraoxa-11,15-dithiapentacosane (12)

To 45 mL of 2-pentanone solution were added the sulfhydryl compound 8 (570 mg, 0.66 mmol), Cs$_2$CO$_3$ (216 mg, 0.66 mmol), and tribromide 11 (75 mg, 0.15 mmol) successively at 0° C. under nitrogen. Then the mixture was brought to reflux at 105° C. overnight until the starting material 11 was completely consumed as monitored by TLC. The reaction mixture was quenched with $H_2O$, extracted with $CH_2Cl_2$, concentrated through rotary evaporation, and purified by flash chromatography using hexane/EtOAc as the eluent to afford compound 12 (270 mg, 0.096 mmol, 64% yield) as a colorless oil: $^1$H NMR (500 MHz, $CDCl_3$) δ 7.25-7.23 (m, 4H), 7.18 (br, 1H), 4.46 (s, 2H), 3.97 (s, 18H), 3.53 (s, 4H), 3.36 (s, 2H), 3.34 (s, 6H), 3.27 (s, 6H), 2.59 (s, 6H), 2.45 (t, J=5.5 Hz, 6H), 1.75-1.69 (m, 6H); $^{13}$C NMR (126 MHz, $CDCl_3$) δ 138.6, 128.5, 127.74, 127.72, 120.4 (q, J=291.8 Hz), 80.1-79.4 (m), 73.3, 72.7, 70.9, 70.2, 69.6, 66.0, 65.5, 46.4, 44.5, 36.7, 30.4, 29.8; $^{19}$F NMR (470 MHz, $CDCl_3$) δ −73.61 (s); MS (MALDI-TOF) m/z 2826 (M+NH$_4$)$^+$.

1-Phenyl-2,5,8,11-tetraoxamidecan-13-ol (14)

To 800 mL of THF were added sodium hydride (16.8 g, 0.42 mol, 60% dispersion in mineral oil) and tetrabutylammonium bromide (11.3 g, 35 mmol) successively at 0° C. Then tetraethylene glycol (121 mL, 0.7 mol) was added dropwise. Afterward, the solution was stirred at room temperature for 1 h and then brought to reflux at 80° C.; benzyl bromide (42 mL, 0.35 mol) was added dropwise to the refluxing mixture. The reaction was quenched by $H_2O$ after 20 h and then extracted with ethyl acetate. The organic phase was concentrated through rotary evaporation and subject to silica gel chromatography using hexane/EtOAc as the eluent to afford compound 14 (71 g, 0.25 mol, 71% yield) as a clear oil: $^1$H NMR (500 MHz, $CDCl_3$) δ 7.27-7.24 (m, 4H), 7.21-7.19 (m, 1H), 4.49 (s, 2H), 3.63-3.56 (m, 14H), 3.51 (t, J=5.0 Hz, 2H), 2.94 (t, J=5.5 Hz, 1H); $^{13}$C NMR (126 MHz, $CDCl_3$) δ 138.2, 128.3, 127.7, 127.5, 73.1, 72.5, 70.58, 70.57, 70.53, 70.3, 69.4, 61.6; MS (ESI) m/z 285 (M+H)$^+$, 307 (M+Na)$^+$, 323 (M+K)$^+$.

17-Bromo-16,16-bis(bromomethyl)-1-phenyl-2,5,8,11,14-pentaoxaheptadecane (15)

To a suspension of sodium hydride (1.2 g, 30 mmol, 60% dispersion in mineral oil) in 60 mL of dry diglyme at 0° C. in a 100 mL flask, equipped with magnetic stirrer and a 60 mL addition funnel, was added a solution of monobenzyl protected tetraethylene glycol 14 (7.7 g, 27 mmol) in 15 mL dry diglyme dropwise under nitrogen atmosphere. The resulting mixture was stirred at 0° C. for 1 h and then at room temperature for another 2 h to give a solution of sodium alcoholate. This alcoholate was added dropwise to the refluxing solution of pentaerythritol tetrabromide 9 (11.6 g, 30 mmol) in 60 mL of diglyme at 165° C. under nitrogen atmosphere. After the addition, the mixture was heated overnight at 165° C. and then cooled to room temperature. The mixture was quenched with $H_2O$. After solvent evaporation, the residue was extracted with EtOAc and washed with $H_2O$, concentrated through rotary evaporation, and subjected to silica gel chromatography using hexane/EtOAc as the eluent to afford compound 15 (9.1 g, 15.4 mmol, 57% yield) as a clear oil: $^1$H NMR (500 MHz, $CDCl_3$) δ 7.20-7.17 (m, 4H), 7.13 (br, 1H), 4.42 (s, 2H), 3.52-3.48 (m, 5H), 3.41-3.40 (m, 9H), 3.39 (s, 8H), 3.22 (s, 2H); $^{13}$C NMR (126 MHz, $CDCl_3$) δ 138.2, 128.2, 127.5, 127.4, 73.0, 71.8, 70.8, 70.51, 70.46, 70.4, 70.2, 69.6, 69.3, 58.8, 43.6, 34.8; MS (ESI) m/z 606 (M+NH$_4$)$^+$, 611 (M+Na)$^+$; HRMS (ESI) calcd for $C_{20}H_{32}Br_3O_5$ 590.9779 (M+H)$^+$, 610.9619 (M+Na)$^+$. found 590.9767, 610.9990, respectively.

28,28,28-Trifluoro-16,16-bis(((3-(3-((1,1,1,3,3,3-hexafluoro-2-(trifluoromethyl)propan-2-yl)oxy)-2,2-bis(((1,1,1,3,3,3-hexafluoro-2-(trifluoromethyl)propan-2-yl)oxy)methyl)propoxy)propyl)thio)methyl)-24,24-bis(((1,1,1,3,3,3-hexafluoro-2-(trifluoromethyl)propan-2-yl)oxy)methyl)-1-phenyl-27,27-bis(trifluoromethyl)-2,5,8,11,14,22,26-heptaoxa-18-thiaoctacosane (16) ($^{19}$F-81)

To 10 mL of 2-pentanone were added the sulfhydryl compound 8 (691 mg, 0.8 mmol), $Cs_2CO_3$ (261 mg, 0.8 mmol), and tribromide 15 (105 mg, 0.18 mmol) successively at 0° C. under nitrogen. Then the mixture was brought to overnight reflux at 105° C. The reaction mixture was quenched with H2O and extracted with $CH_2Cl_2$, concentrated through rotary evaporation, and purified by silica gel chromatography using hexane/EtOAc as the eluent to afford compound 16 (270 mg, 0.092 mmol, 52% yield) as a clear oil: $^1$H NMR (500 MHz, $CDCl_3$) δ 7.25-7.23 (m, 4H), 7.19-7.18 (m, 1H), 4.48 (s, 2H), 3.97 (s, 18H), 3.49 (d, J=4.5 Hz, 2H), 3.37 (t, J=7.0 Hz, 6H), 3.31 (s, 2H), 3.29 (s, 6H), 2.58 (s, 6H), 2.46 (t, J=6.0 Hz, 6H), 1.74 (t, J=7.0 Hz, 6H); $^{13}$C NMR (126 MHz, $CDCl_3$) δ 138.6, 128.5, 127.9, 127.8, 120.4 (q, J=294.0 Hz), 80.4-79.1 (m), 73.5, 72.7, 70.92, 70.90, 70.88, 70.81, 70.5, 70.2, 69.7, 66.1, 65.7, 46.4, 44.5, 36.7, 30.4, 29.8; $^{19}$F NMR (470 MHz, $CDCl_3$) δ −73.38 (s); MS (ESI) m/z 2965 (M+Na)$^+$, 2981 (M+K)$^+$.

2-(2-(2-(Benzyloxy)ethoxy)ethoxy)ethanol (18)

The procedure was the same as the synthesis of compound 14. From 150 g of 17 (1 mol), 16 g of sodium hydride (0.4 mol, 60% dispersion in mineral oil), 62.2 g of benzyl bromide (0.36 mol), 23.4 g of tetrabutylammonium bromide (72.8 mmol) afforded 68 g of 18 (0.28 mol, 78% yield) as a clear oil: $^1$H NMR (500 MHz, $CDCl_3$) δ 7.34-7.28 (m, 4H), 7.27-7.26 (m, 1H), 4.56 (s, 2H), 3.71-3.66 (m, 8H), 3.63-3.60 (m, 2H), 3.59 (s, 2H), 2.76 (t, J=6.0 Hz, 1H); $^{13}$C NMR (126 MHz, $CDCl_3$) δ 138.3, 128.5, 127.9, 127.8, 73.4, 72.7, 70.8, 70.7, 70.5, 69.5, 61.8; MS (ESI) m/z 241 (M+H)$^+$, 263 (M+Na)$^+$, 279 (M+K)$^+$.

14-Bromo-13,13-bis(bromomethyl)-1-phenyl-2,5,8,11-tetraoxatetradecane (19)

The procedure was the same as the synthesis of compound 15. From 4.4 g of 18 (18.2 mmol), 0.84 g of sodium hydride (21 mmol, 60% dispersion in mineral oil), and 7.74 g of 9 (20 mmol) afforded 6.1 g of 19 (11.2 mmol, 61% yield) as a light yellow oil: $^1$H NMR (500 MHz, $CDCl_3$) δ 7.32 (br, 4H), 7.26 (br, 1H), 4.55 (s, 2H), 3.67-3.62 (m, 12H), 3.51 (s, 8H); $^{13}$C NMR (126 MHz, $CDCl_3$) δ 138.2, 128.3, 127.6, 127.5, 73.1, 70.9, 70.7, 70.63, 70.58, 70.3, 69.7, 69.4, 43.7, 34.9; MS (ESI) m/z 566 (M+Na)$^+$; HRMS (ESI) calcd for $C_{18}H_{28}Br_3O_4$ 546.9517 (M+H)$^+$. found 546.9536.

25,25,25-Trifluoro-13,13-bis(((3-(3-((1,1,1,3,3,3-hexafluoro-2-(trifluoromethyl)propan-2-yl)oxy)-2,2-bis(((1,1,1,3,3,3-hexafluoro-2-(trifluoromethyl)propan-2-yl)oxy)methyl)propoxy)propyl)thio)-methyl)-21,21-bis(((1,1,1,3,3,3-hexafluoro-2-(trifluoromethyl)propan-2-yl)oxy)methyl)-1-phenyl-24,24-bis(trifluoromethyl)-2,5,8,11,19,23-hexaoxa-15-thiapentacosane (20)

The procedure was the same as the synthesis of compound 12. From 548 mg of 19 (1 mmol), 4 g of compound 8 (4.5 mmol), and 1.5 g of Cs2CO3 (4.5 mmol) afforded 1.7 g of 20 as a clear oil (0.59 mmol, 59% yield): $^1$H NMR (500 MHz, CDCl$_3$) δ 7.34-7.32 (m, 4H), 7.28-7.27 (m, 1H), 4.57 (s, 2H), 4.06 (s, 18H), 3.68-3.62 (m, 10H), 3.59 (d, J=4.5 Hz, 2H), 3.46 (t, J=6.5 Hz, 6H), 3.41 (s, 2H), 3.38 (s, 6H), 2.67 (s, 6H), 2.56 (t, J=7.5 Hz, 6H), 1.87-1.80 (m, 6H); $^{13}$C NMR (126 MHz, CDCl$_3$) δ 138.6, 128.6, 127.9, 127.8, 120.4 (q, J=293.6 Hz), 80.4-79.2 (m), 73.5, 72.8, 71.0, 70.97, 70.88, 70.63, 70.61, 70.27, 70.23, 69.73, 69.71, 66.1, 65.7, 65.62, 65.60, 65.58, 46.5, 44.5, 36.7, 30.4, 29.9; $^{19}$F NMR (470 MHz, CDCl$_3$) δ −73.27 (s); MS (ESI) m/z 2920.8 (M+Na)$^+$.

2-(2-(2-(Trityloxy)ethoxy)ethoxy)ethanol (21)

To a CH$_2$Cl$_2$ (300 mL) solution of triethylene glycol (21 g, 140 mmol) was added Et$_3$N (20 mL, 140 mmol); then trityl chloride (19.5 g, 70 mmol) in CH$_2$Cl$_2$ (100 mL) was added dropwise at 0° C. The mixture was stirred overnight and quenched with H$_2$O. The organic phase was washed with H$_2$O and brine successively, concentrated through rotary evaporation, and subjected to silica gel chromatography using hexane/EtOAc as the eluent to afford compound 21 (21 g, 53.6 mmol, 77% yield) as a clear liquid: $^1$H NMR (500 MHz, CDCl$_3$) δ 7.47-7.46 (m, 6H), 7.28 (t, J=7.0 Hz, 6H), 7.21 (t, J=7.0 Hz, 3H), 3.68 (s, 8H), 3.60 (br, 2H), 3.25 (br, 2H), 2.57 (br, 1H); $^{13}$C NMR (126 MHz, CDCl$_3$) δ 144.2, 128.8, 127.9, 127.1, 86.8, 72.7, 71.0, 70.8, 70.7, 63.4, 61.9; MS (ESI) m/z 415 (M+Na)$^+$.

14-Bromo-13,13-bis(bromomethyl)-1,1,1-triphenyl-2,5,8,11-tetraoxatetradecane (22)

The procedure was the same as synthesis of compound 15. From 9.3 g (24 mmol) of 9, 7.84 g (20 mmol) of 21, and 0.92 g of NaH (60% dispersion in mineral oil, 23 mmol) afforded 7.9 g of 22 (11.3 mmol, 56% yield) as a clear oil: $^1$H NMR (500 MHz, CDCl$_3$) δ 7.47-7.46 (m, 6H), 7.27 (t, J=8.5 Hz, 6H), 7.20 (t, J=8.0 Hz, 3H), 3.68-3.63 (m, 10H), 3.51 (s, 2H), 3.49 (s, 6H), 3.24 (t, J=4.5 Hz, 2H); $^{13}$C NMR (126 MHz, CDCl$_3$) δ 144.2, 128.8, 127.8, 127.0, 86.6, 71.09, 70.96, 70.82, 70.80, 70.5, 69.9, 63.5, 43.9, 35.0; MS (ESI) m/z 719 (M+Na)$^+$, 243 (Ph$_3$C)+; HRMS (ESI) calcd for C$_{30}$H$_{35}$Br$_3$NaO$_4$ 720.9963 (M+Na)$^+$. found 720.9959.

25,25,25-Trifluoro-13,13-bis(((3-(3-((1,1,1,3,3,3-hexafluoro-2-(trifluoromethyl)propan-2-yl)oxy)-2,2-bis(((1,1,1,3,3,3-hexafluoro-2-(trifluoromethyl)propan-2-yl)oxy)methyl)propoxy)propyl)thio)methyl)-21,21-bis(((1,1,1,3,3,3-hexafluoro-2-(trifluoromethyl)propan-2-yl)oxy)methyl)-1,1,1-triphenyl-24,24-bis(trifluoromethyl)-2,5,8,11,19,23-hexaoxa-15-thiapentacosane (23)

The procedure was the same as synthesis of compound 16. From 14 g (16 mmol) of 8, 3.1 g (4.4 mmol) of 22, and 5.8 g of Cs$_2$CO$_3$ (17.8 mmol) afforded 12 g of 23 (3.93 mmol, 89% yield) as a clear oil: $^1$H NMR (500 MHz, CDCl$_3$) δ 7.48-7.46 (m, 6H), 7.30-7.25 (m, 6H), 7.23-7.21 (m, 3H), 4.04 (s, 18H), 3.66-3.64 (m, 8H), 3.58 (s, 2H), 3.44 (s, 6H), 3.39 (s, 2H), 3.36 (s, 6H), 3.24 (s, 2H), 2.65 (s, 6H), 2.54-2.53 (m, 6H), 1.82-1.81 (m, 6H); $^{13}$C NMR (126 MHz, CDCl$_3$) δ 144.4, 129.0, 128.0, 127.1, 120.4 (q, J=293.8 Hz), 86.8, 80.1-79.4 (m), 72.8, 71.1, 70.96, 70.94, 70.85, 70.6, 70.3, 66.1, 65.7, 65.6, 63.6, 46.4, 44.5, 36.7, 30.4, 29.8; $^{19}$F NMR (470 MHz, CDCl$_3$) δ −73.61 (s); MS (ESI) m/z 3073 (M+Na)$^+$.

Compound 24

To a solution of 23 (11.6 g, 3.8 mmol) in DCM (400 mL) was added TFA (5.8 mL, 76 mmol) dropwise at 0° C. After the starting material was consumed completely as monitored by TLC, the solvent was removed through rotary evaporation and the residue was subjected to silica gel chromatography using hexane/EtOAc as the eluent to afford compound 24 (9.1 g, 3.24 mmol, 85% yield) as a viscous liquid: $^1$H NMR (500 MHz, CDCl$_3$) δ 4.06 (s, 18H), 3.72 (t, J=4.0 Hz, 2H), 3.66-3.59 (m, 10H), 3.46 (t, J=7.5 Hz, 6H), 3.42 (s, 2H), 3.38 (s, 6H), 2.68 (s, 6H), 2.60 (br, 1H), 2.56 (t, J=7.5 Hz, 6H), 1.86-1.81 (m, 6H); $^{13}$C NMR (126 MHz, CDCl$_3$) δ 120.4 (q, J=293.6 Hz), 80.4-79.2 (m), 72.9, 72.7, 70.87, 70.84, 70.80, 70.64, 70.3, 66.1, 65.7, 61.9, 46.4, 44.5, 36.7, 30.4, 29.9; $^{19}$F NMR (470 MHz, CDCl$_3$) δ −73.34 (s); MS (APCI) m/z 2808 (M+2H)$^+$, 2658 (M−HOCH$_2$CH$_2$OCH$_2$CH$_2$OCH$_2$CH$_2$O+H)$^+$.

Mesylate 25

Et$_3$N (0.59 mL, 4.2 mmol) and methanesulfonyl chloride (0.33 mL, 4.2 mmol) were added to a solution of compound 24 (4.75 g, 1.7 mmol) dissolved in THF (40 mL) and anhydrous CH$_2$Cl$_2$ (40 mL) mixed solvent at 0° C. The reaction mixture was then stirred at room temperature overnight. The reaction was quenched with water and extracted with CH$_2$Cl$_2$. Evaporation of the solvent by rotary evaporation followed by flash chromatography on silica gel using hexane/EtOAc as the eluent afforded the product mesylate 25 (3.7 g, 1.28 mmol, 76% yield) as a colorless oil: $^1$H NMR (500 MHz, CDCl$_3$) δ 4.38 (s, 2H), 4.06 (s, 18H), 3.77 (s, 2H), 3.66-3.58 (m, 8H), 3.47 (s, 6H), 3.41 (s, 2H), 3.38 (s, 6H), 3.08 (s, 3H), 2.67 (s, 6H), 2.56-2.55 (m, 6H), 1.84 (s, 6H); $^{13}$C NMR (126 MHz, CDCl$_3$) δ 120.4 (q, J=294.2 Hz), 80.1-79.4 (m), 72.9, 71.0, 70.9, 70.8, 70.6, 70.2, 69.4, 69.3, 66.1, 65.7, 65.6, 46.4, 44.5, 37.8, 36.7, 30.4, 29.9; $^{19}$F NMR (470 MHz, CDCl$_3$) δ −73.45 (s); MS (APCI) m/z 2885 (M+H)$^+$, 2821 (M−SO$_2$+H)$^+$, 2657 (M−MsOCH$_2$CH$_2$OCH$_2$CH$_2$OCH$_2$CH$_2$O)$^+$.

Thioacetate 26

To a solution of mesylate 25 (3.6 g, 1.25 mmol) in THF (14 mL) and DMSO (14 mL) mixed solvents was added potassium thioacetate (0.5 g, 4.38 mmol), and the reaction mixture was stirred at 120° C. overnight. The reaction mixture was extracted with DCM, washed with water and brine successively, concentrated through rotary evaporation, and subjected to silica gel chromatography using hexane/EtOAc as the eluent to afford the thioester 26 (3.12 g, 1.09 mmol, 87% yield) as a light yellow oil: $^1$H NMR (500 MHz, CDCl$_3$) δ 4.06 (s, 18H), 3.63-3.60 (m, 10H), 3.47 (t, J=6.5 Hz, 6H), 3.42 (s, 2H), 3.39 (s, 6H), 3.11 (t, J=7.0 Hz, 2H), 2.68 (s, 6H), 2.57 (t, J=6.5 Hz, 6H), 2.34 (s, 3H), 1.84 (t, J=7.0 Hz, 6H); $^{13}$C NMR (126 MHz, CDCl$_3$) δ 120.3 (q, J=293.8 Hz), 80.1-79.4 (m), 72.7, 71.8, 70.7, 70.60, 70.57, 70.2, 70.0, 66.0, 65.6, 46.4, 44.4, 36.7, 30.6, 30.4, 29.8, 29.0; $^{19}$F NMR (470 MHz, CDCl$_3$) δ −73.62 (s); MS (MALDI-TOF) m/z 2881.1 (M+Na)$^+$, 2904.7 (M+K)$^+$.

Free Thiol Compound 27

The procedure was the same as the synthesis of compound 8. From 3 g (1.05 mmol) of 26 and 0.12 g (3.15 mmol) of LiAlH$_4$ afforded 2.6 g of 27 (0.92 mmol, 88% yield) as a clear oil: $^1$H NMR (500 MHz, CDCl$_3$) δ 4.06 (s, 18H), 3.63-3.59 (m, 10H), 3.46 (t, J=6.0 Hz, 6H), 3.41 (s, 2H), 3.36 (s, 6H), 2.71-2.67 (m, 8H), 2.55 (t, J=6.0 Hz, 6H), 1.83 (t, J=7.0 Hz, 6H), 1.60 (t, J=7.0 Hz, 1H); $^{13}$C NMR (126 MHz, CDCl$_3$) δ 120.4 (q, J=297.4 Hz), 80.4-79.2 (m), 73.1, 72.8, 70.9, 70.8, 70.7, 70.6, 70.3, 66.1, 65.7, 46.4, 44.5, 36.7, 30.4, 29.9, 24.5;

$^{19}$F NMR (470 MHz, CDCl$_3$) δ −73.59 (s); MS (APCI) m/z 2824 (M+2H)$^+$, 2763 (M−HSCH$_2$CH$_2$+H)$^+$, 2657 (M−HSCH$_2$CH$_2$OCH$_2$CH$_2$OCH$_2$CH$_2$O)$^+$.

2-(2-((Tetrahydro-2H-pyran-2-yl)oxy)ethoxy)ethanol (28)

To 800 mL of CH$_2$Cl$_2$ were added diethylene glycol (57 mL, 0.6 mol) and p-toluenesulfonic acid monohydrate (5.7 g, 30 mmol) successively. Then tetrahydropyran (27.4 mL, 0.3 mol) was added dropwise at 0° C. The reaction mixture was stirred overnight and quenched with H2O, extracted with CH$_2$Cl$_2$, washed with H$_2$O and brine successively, concentrated through rotary evaporation, and subjected to silica gel chromatography using CH$_2$Cl$_2$/MeOH as the eluent to afford compound 28 (32.5 g, 0.17 mol, 57% yield) as a clear oil: $^1$H NMR (500 MHz, CDCl$_3$) δ 4.59 (t, J=4.0 Hz, 1H), 3.85-3.80 (m, 2H), 3.68-3.64 (m, 4H), 3.59-3.55 (m, 3H), 3.48-3.44 (m, 1H), 2.98 (br, 1H), 1.81-1.76 (m, 1H), 1.71-1.65 (m, 1H), 1.59-1.46 (m, 4H).

2,2′-((8-(15-Phenyl-2,5,8,11,14-pentaoxapentadecyl)-8-((2-(2-((tetrahydro-2H-pyran-2-yl)oxy)ethoxy)-ethoxy)methyl)-3,6,10,13-tetraoxapentadecane-1,15-diyl)bis(oxy))bis(tetrahydro-2H-pyran) (29)

To a suspension of sodium hydride (0.72 g, 18 mmol, 60% dispersion in mineral oil) in 20 mL of dry diglyme at 0° C. in a 100 mL flask, equipped with a magnetic stirrer and an addition funnel, was added a solution of monotetrahydropyranyl protected diethylene glycol 28 (3.42 g, 18 mmol) in 8 mL dry diglyme dropwise under nitrogen atmosphere. The resulting mixture was stirred at 0° C. for 1 h and then at room temperature for another 2 h to give a solution of sodium alcoholate. This alcoholate was added dropwise to the refluxing solution of compound 15 (2.36 g, 4 mmol) in 10 mL of diglyme under nitrogen atmosphere at 165° C. Afterward, the mixture was heated at reflux overnight and then cooled to room temperature. The mixture was quenched with H$_2$O. After solvent evaporation through rotary evaporation, the mixture was extracted with EtOAc and washed with H$_2$O and brine, concentrated through rotary evaporation, and subjected to silica gel chromatography using hexane/EtOAc as the eluent to afford compound 29 (1.9 g, 2.07 mmol, 52% yield) as a clear oil: $^1$H NMR (500 MHz, CDCl$_3$) δ 7.36-7.35 (m, 4H), 7.29 (br, 1H), 4.58 (s, 2H), 3.75 (t, J=6.0 Hz, 6H), 3.68-3.60 (m, 16H), 3.50-3.45 (m, 14H); $^{13}$C NMR (126 MHz, CDCl$_3$) δ 138.4, 128.5, 127.8, 127.7, 98.9, 73.2, 71.05, 70.98, 70.66, 70.63, 70.61, 70.58, 70.56, 70.50, 70.4, 70.3, 70.0, 69.4, 66.7, 62.1, 45.6, 30.6, 25.4, 19.5; MS (ESI) m/z 937 (M+NH$_4$)$^+$, 942 (M+Na)$^+$, 958 (M+K)$^+$; HRMS (ESI) calcd for C$_{47}$H$_{86}$NO$_{17}$ 936.5896 (M+NH$_4$)$^+$. found 936.5895.

23-Bromo-16,16-bis((2-(2-bromoethoxy)ethoxy)methyl)-1-phenyl-2,5,8,11,14,18,21-heptaoxatricosane (30)

To a stirred solution of compound 29 (500 mg, 0.54 mmol) in 1 The resulting mixture was stirred at room temperature overnight. The mixture was diluted with CH$_2$Cl$_2$ and washed with water. The CH$_2$Cl$_2$ layer was separated, dried over Na$_2$SO$_4$, and concentrated through rotary evaporation. The residue was purified by chromatography on silica gel using hexane/EtOAc as the eluent to give tribromide 30 (320 mg, 0.37 mmol, 69% yield) as a yellow oil: $^1$H NMR (500 MHz, CDCl$_3$) δ 7.32 (s, 4H), 7.26 (s, 1H), 4.54 (s, 2H), 3.79-3.77 (m, 6H), 3.64-3.59 (m, 20H), 3.55 (s, 8H), 3.44 (s, 14H); $^{13}$C NMR (126 MHz, CDCl$_3$) δ 138.2, 128.3, 127.6, 127.5, 73.1, 71.08, 71.02, 70.96, 70.61, 70.58, 70.55, 70.52, 70.32, 70.28, 69.93, 69.87, 69.4, 45.5, 30.6; MS (ESI) m/z 874 (M+Na)$^+$; HRMS (ESI) calcd for C$_{32}$H$_{59}$Br$_3$NO$_{ii}$ 872.1618 (M+NH$_4$)$^+$. found 872.1610.

Compound 31 ($^{19}$F-243)

To 10 mL of 2-pentanone solution were added the sulfhydryl compound 27 (290 mg, 0.1 mmol), Cs$_2$CO$_3$ (49 mg, 0.15 mmol), and tribromide 30 (21 mg, 0.025 mmol) successively at 0° C. under nitrogen. Then the mixture was brought to reflux at 105° C. overnight until the starting material 30 was completely consumed as monitored by TLC. The reaction mixture was quenched with H$_2$O and extracted with CH$_2$Cl$_2$, concentrated through rotary evaporation, and purified by flash silica gel chromatography using hexane/EtOAc as the eluent to afford compound 31 (190 mg, 0.021 mmol, 82% yield) as a clear oil: $^1$H NMR (500 MHz, CDCl$_3$) δ 7.30 (br, 3H), 7.24 (s, 2H), 4.53 (s, 2H), 4.00 (s, 54H), 3.63-3.51 (m, 64H), 3.41 (s, 26H), 3.36-3.33 (m, 24H), 2.71-2.69 (m, 12H), 2.62 (s, 18H), 2.50 (s, 18H), 1.78 (s, 18H); $^{13}$C NMR (126 MHz, CDCl$_3$) δ 139.2, 137.2, 128.6, 127.9, 120.3 (q, J=294.0 Hz), 72.7, 71.15, 71.12, 70.87, 70.84, 70.80, 70.73, 70.70, 70.59, 70.55, 70.50, 70.34, 70.27, 70.23, 69.65, 66.0, 65.6 46.4, 44.4, 36.7, 32.2, 32.0, 30.4, 29.9, 29.8; $^{19}$F NMR (470 MHz, CDCl$_3$) δ −74.16 (s); MS (MALDI-TOF) m/z 9105 (M+Na)$^+$.

17-Iodo-16,16-bis(iodomethyl)-1-phenyl-2,5,8,11,14-pentaoxaheptadecane (32)

To an acetone solution (15 mL) of compound 15 (1.18 g, 2 mmol) was added sodium iodide (4.5 g, 30 mmol), then the solution was brought to reflux at 65° C. for 3 days. The solvent was removed through rotary evaporation, and the residue was purified by silica gel chromatography using hexane/EtOAc as the eluent to afford compound 32 as a yellow oil: $^1$H NMR (500 MHz, CDCl$_3$) δ 7.35 (br, 4H), 7.29 (br, 1H), 4.58 (s, 2H), 3.68-3.65 (m, 16H), 3.52 (s, 2H), 3.37 (s, 6H); $^{13}$C NMR (126 MHz, CDCl$_3$) δ 138.3, 128.4, 127.7, 127.6, 73.2, 71.6, 71.0, 70.70, 70.68, 70.66, 70.4, 69.5, 39.6, 11.8; MS (ESI) m/z 750 (M+NH$_4$)$^+$, 755 (M+Na)$^+$, 771 (M+K)$^+$; HRMS (ESI) calcd for C$_{20}$H$_{32}$I$_3$O$_5$ 732.9384 (M+H)$^+$, 749.9644 [M+NH$_4$]+. found 732.9405, 749.9655, respectively.

2-((Tetrahydro-2H-pyran-2-yl)oxy)ethanol (33)

The procedure was the same as the synthesis of compound 28. From 62 g of ethylene glycol (1 mol), 9.5 g of p-toluenesulfonic acid monohydrate (50 mmol), and 28 g of tetrahydropyran (333 mmol) afforded 33 (30 g, 205 mmol, 62% yield) as a clear oil: $^1$H NMR (500 MHz, CDCl$_3$) δ 4.53 (d, J=3.0 Hz, 1H), 3.87-3.84 (m, 1H), 3.75-3.61 (m, 4H), 3.49-3.47 (m, 1H), 3.15 (br, 1H), 1.82-1.79 (m, 1H), 1.78-1.68 (m, 1H), 1.55-1.46 (m, 4H); MS (ESI) m/z 169 (M+Na)$^+$.

2-((1-Phenyl-16,16-bis((2-((tetrahydro-2H-pyran-2-yl)oxy)ethoxy)methyl)-2,5,8,11,14,18-hexaoxaicosan-20-yl)oxy)tetrahydro-2H-pyran (34)

To a suspension of sodium hydride (0.64 g, 16 mmol, 60% dispersion in mineral oil) in 30 mL of dry diglyme at 0° C. in a 100 mL flask, equipped with a magnetic stirrer and an addition funnel, was added a solution of monotetrahydropyranyl protected ethylene glycol 33 (2.34 g, 16 mmol) in 8 mL of dry diglyme dropwise under nitrogen atmosphere. The resulting mixture was stirred at 0° C. for 1 h and then at room temperature for another 2 h to give a solution of sodium alcoholate. This alcoholate was added dropwise to the 165° C. refluxing solution of pentaerythritol tribromide 15 (2.36 g, 4 mmol) in 15 mL of diglyme under nitrogen atmosphere. Afterward, the mixture was kept refluxing at 165° C. overnight and then cooled to room temperature. The reaction mixture was quenched with $H_2O$ and, after solvent evaporation, extracted with EtOAc and washed with $H_2O$, concentrated through rotary evaporation, and subjected to silica gel chromatography using $CH_2Cl_2$/MeOH as the eluent to afford compound 34 (0.7 g, 0.89 mmol, 22% yield) as a clear oil: $^1H$ NMR (500 MHz, $CDCl_3$) δ 7.28 (br, 4H), 7.21 (br, 1H), 4.59 (s, 3H), 4.51 (s, 2H), 3.84-3.80 (m, 2H), 3.75-3.73 (m, 2H), 3.61-3.59 (m, 12H), 3.52-3.42 (m, 12H), 3.37-3.35 (m, 14H), 1.79-1.77 (m, 3H), 1.67-1.63 (m, 3H), 1.53-1.46 (m, 12H); $^{13}C$ NMR (126 MHz, $CDCl_3$) δ 138.2, 128.2, 127.6, 127.4, 98.5, 73.1, 71.0, 70.8, 70.61, 70.58, 70.57, 70.55, 70.54, 70.3, 70.0, 69.9, 69.4, 66.3, 61.7, 45.6, 30.5, 25.4, 19.3; MS (ESI) m/z 804.5 $(M+NH_4)^+$; HRMS (ESI) calcd for $C_{41}H_{74}NO_{14}$ 804.5109 $(M+NH_4)^+$. found 804.5112.

20-Bromo-16,16-bis((2-bromoethoxy)methyl)-1-phenyl-2,5,8,11,14,18-hexaoxaicosane (35)

To a stirred solution of monotetrahydropyranyl protected ethylene glycol 34 (260 mg, 0.33 mmol) in 5 mL of $CH_2Cl_2$ was added triphenylphosphine dibromide (627 mg, 1.49 mmol) at 0° C. The resulting mixture was stirred at room temperature overnight. The mixture was diluted with $CH_2Cl_2$ and washed with water. The $CH_2Cl_2$ layer was separated, dried over $Na_2SO_4$, and concentrated through rotary evaporation. The residue was purified by silica gel chromatography using $CH_2Cl_2$/MeOH as the eluent to give compound 35 (205 mg, 0.28 mmol, 86% yield) as a yellow oil: $^1H$ NMR (500 MHz, $CDCl_3$) δ 7.36-7.35 (m, 4H), 7.29 (br, 1H), 4.58 (s, 2H), 3.75 (t, J=6.0 Hz, 6H), 3.68-3.60 (m, 16H), 3.50-3.45 (m, 14H); $^{13}C$ NMR (126 MHz, $CDCl_3$) δ 138.4, 128.5, 127.8, 127.7, 73.3, 71.3, 71.1, 70.81, 70.78, 70.75, 70.69, 70.5, 69.6, 69.5, 69.4, 45.9, 30.9; MS (ESI) m/z 738 $(M+NH_4)+$, 743 $(M+Na)^+$; HRMS (ESI) calcd for $C_{26}H_{44}Br_3O_8$ 723.0566 $(M+H)^+$, 740.0831 $(M+NH_4)^+$. found 723.0592, 740.0802, respectively.

Reaction Between Compounds 35 and 27

To 6 mL of 2-pentanone were added the sulfhydryl compound 27 (160 mg, 0.057 mmol), $Cs_2CO_3$ (23 mg, 0.07 mmol), and tribromide 35 (10 mg, 0.014 mmol) successively at 0° C. under nitrogen. Then the mixture was brought to overnight reflux at 105° C. until the starting material 35 was completely consumed as monitored by TLC. The reaction mixture was quenched with $H_2O$, extracted with $CH_2Cl_2$, concentrated through rotary evaporation, and purified by flash silica gel chromatography using hexane/EtOAc as the eluent to afford a mixture of 59 mg as a clear oil. $^{19}F$ NMR showed a ratio 2/1 two peaks. $^{19}F$ NMR (470 MHz, $CDCl_3$) δ −73.72 (s), −74.28 (s).

REFERENCES

The contents of all references are incorporated by reference herein for all purposes.
1. Knapen, J. W. J.; van der Made, A. W.; de Wild, J. C.; van Leeuwen, P. W. N. M.; Wijkens, P.; Grove, D. M.; van Koten, G., Homogeneous catalysts based on silane dendrimers functionalized with arylnickel(II) complexes, *Nature* 1994, 372, 659-663.
2. Cooper, A. I.; Londono, J. D.; Wignall, G.; McClain, J. B.; Samulski, E. T.; Lin, J. S.; Dobrynin, A.; Rubinstein, M.; Burke, A. L. C.; Fréchet, J. M. J.; DeSimone, J. M., Extraction of a hydrophilic compound from water into liquid CO2 using dendritic surfactants, *Nature* 1997, 389, 368-371.
3. Percec, V.; Ahn, C.-H.; Ungar, G.; Yeardley, D. J. P.; Möller, M.; Sheiko, S. S., Controlling polymer shape through the self-assembly of dendritic side-groups, *Nature* 1998, 391, 161-164.
4. Percec, V.; Glodde, M.; Bera, T. K.; Miura, Y.; Shiyanovskaya, I.; Singer, K. D.; Balagurusamy, V. S. K.; Heiney, P. A.; Schnell, I.; Rapp, A.; Spiess, H.-W.; Hudson, S. D.; Duan, H., Self-organization of supramolecular helical dendrimers into complex electronic materials, *Nature* 2002, 419, 384-387.
5. Criscione, J. M.; Le, B. L.; Stern, E.; Brennan, M.; Rahner, C.; Papademetris, X.; Fahmy, T. M., Self-assembly of pH-responsive fluorinated dendrimer-based particulates for drug delivery and noninvasive imaging., *Biomaterials* 2009, 30, 3946-3955.
6. Sonke, S.; Tomalia, D. A., *Adv. Drug Delivery Rev.* 2005, 57, 2106-2129
7. Astruc, D.; Boisselier, E.; Ornelas, C., Dendrimers Designed for Functions: From Physical, Photophysical, and Supramolecular Properties to Applications in Sensing, Catalysis, Molecular Electronics, Photonics, and Nanomedicine, *Chem. Rev.* 2010, 110, 1857-1959.
8. Frechet, J. M. J., Functional polymers and dendrimers: reactivity, molecular architecture, and interfacial energy, *Science* 1994, 263, 1710-1715
9. Tomalia, D. A., J., In quest of a systematic framework for unifying and defining nanoscience, *J. Nanopart. Res.* 2009, 11, 1251-1310.
10. Caminade, A. M.; Turrin, C. O.; Supra, P.; Majoral, J. P., Fluorinated dendrimers, *Curr. Opin. Colloid Interface Sci.* 2003, 8, 282-295.
11. Grayson, S. M.; Fréchet, J. M. J., Convergent Dendrons and Dendrimers: from Synthesis to Applications, *Chem. Rev.* 2001, 101, 3819-3868.
12. Bryant, L. H., Jr.; Brechbiel, M. W.; Wu, C.; Bulte, J. W. M.; Herynek, V.; Frank, J. A. J., Synthesis and relaxometry of high-generation (G=5, 7, 9, and 10) PAMAM dendrimer-DOTA-gadolinium chelates, *Magn. Reson. Imaging* 1999, 9, 348-352.
13. Wooley, K. L.; Hawker, C. J.; Fréhet, J. M. J., Hyperbranched macromolecules via a novel double-stage convergent growth approach, *J. Am. Chem. Soc.* 1991, 113, 4252-4261.
14. Kawaguchi, T.; Walker, K. L.; Wilkins, C. L.; Moore, J. S., Double Exponential Dendrimer Growth, *J. Am. Chem. Soc.* 1995, 117, 2159-2165.
15. Eloy, C., *Phys. Rev. Lett.* 2011, 107, 258101-1-258101-5.
16. Jiang, Z.-X.; Liu, X.; Jeong, E.-K.; Yu, Y. B., Symmetry-Guided Design and Fluorous Synthesis of a Stable and Rapidly Excreted Imaging Tracer for 19F MRI, *Angew. Chem., Int. Ed.* 2009, 48, 4755-4758.
17. Newkome, G. R.; Shreiner, C., Dendrimers Derived from 1→3 Branching Motif, *Chem. Rev.* 2010, 110, 6338-6442.
18. Jiang, Z.-X.; Yu, Y. B., Fluorous mixture synthesis of asymmetric dendrimers, *J. Org. Chem.* 2010, 75, 2044-2049.
19. Uneyam, K., Organofluorine Chemistry; Blackwell: Ames, Iowa, 2006.

20. Jiang, Z.-X.; Yu, Y. B., The synthesis of a geminally perfluoro-tert-butylated β-amino acid and its protected forms as a potential pharmacokinetic modulator and reporter for peptide-based pharmaceuticals, *J. Org. Chem.* 2007, 72, 1464-1467.
21. Jiang, Z.-X.; Yu, Y. B., The design and synthesis of highly branched and spherically symmetric fluorinated oils and amphiles, Tetrahedron 2007, 63, 3982-3988.
22. Szabó, D.; Mohl, J.; Bálint, A.-M.; Bodor, A.; Rábai, J. *J. Fluorine Chem.* 2006, 127, 1496-1504.
23. Nemes, A.; Tölgyesi, L.; Bodor, A.; Rábai, J.; Szabó, D., Greener fluorous chemistry: Convenient preparation of new types of CF3-rich secondary alkyl mesylates and their use for the synthesis of azides, amines, imidazoles and imidazolium salts, *J. Fluorine Chem.* 2010, 131, 1368-1376.
24. Xu, Z.; Moore, J. S. *Angew. Chem., Int. Ed. Engl.* 1993, 32, 1354-1357.
25. Svergun, D. I. *J. Appl. Crystallogr.* 1992, 25, 495-503.
26. Svergun, D. I., Restoring low resolution structure of biological macromolecules from solution scattering using simulated annealing, *Biophys. J.* 1999, 76, 2879-2886.
27. Kozin, M. B.; Svergun, D. I., Restoring low resolution structure of biological macromolecules from solution scattering using simulated annealing, *J. Appl. Crystallogr.* 2001, 34, 33-41.
28. Konarev, P. V.; Volkov, V. V.; Sokolova, A. V.; Koch, M. H. J.; Svergun, D. I. *J Appl Cryst.,* 2003, 36, 1277-1282.
29. Whitten, A.; Trewhella, J. Small-Angle Scattering and Neutron Contrast Variation. In: Micro and Nano Technologies in Bioanalysis. New York: Humana, 2009, pp. 307-322.
30. Franke, D.; Svergun, D. I. J. Appl. Cryst., 2009, 42, 342-346.
31. Volkov, V. V.; Svergun, D. I. J. Appl. Cryst., 2003, 36, 860-864.

That which is claimed is:

1. A dendrimer comprising a generation (G) branching structure comprising a core, branches and periphery ends, wherein length of the branches increases exponentially from the periphery ends to the core and the number of branches increases exponentially from the core to the periphery ends, wherein the number of branches in a nth layer is defined as $m_n$ and the number of bonds between the nth layer and n−1 layer is defined as $l_n$, wherein n is defined as a value of $1 \leq n \leq G$, wherein the increasing number of $m_n$ from the core to the periphery is defined by the formula $m_n = a \times m_{n-1}$ and the increasing number of $l_n$ from the periphery to the core is defined by the formula $l_{n-1} = b \times l_n$, wherein a is a branch multiplier for growing the number of branches and b is the branch length multiplier for growth of the length of the branches and wherein the length multiplier b satisfies $1 \leq b \leq a$.

2. The dendrimer according to claim 1, wherein a has an integer value and b has an integer or non-integer value.

3. The dendrimer according to claim 2, wherein the value of a and b remain constant.

4. The dendrimer according to claim 1, wherein the dendrimer exhibits a proportionality constant wherein the proportionality constant is defined by the following formula:

$$c = \frac{b-1}{a-1} \times 100\%. \quad (1)$$

5. The dendrimer according to claim 4, wherein the proportionality constant is greater than 2%.

6. The dendrimer according to claim 1, wherein $l_n$ is an integer.

7. The dendrimer according to claim 1, wherein the value of $l_{n-1}$ floats between $[bl_n-1, bl_n+1]$ and is an integer.

8. The dendrimer according to claim 1, where the branch multiplicity a has a value of 2, 3, 4 or 5.

9. The dendrimer according to claim 1, wherein the branch length multiplier b has a non-integer value and the value of $l_{n-1}$ floats between $[bl_n-1, bl_n+1]$ and is an integer.

10. The dendrimer according to claim 1, wherein the branch length multiplier b has a value of 2 or greater while remaining less than or equal to a.

11. The dendrimer according to claim 1, wherein the periphery ends comprise attachment sites for a terminal functional group.

12. The dendrimer according to claim 11, wherein the terminal functional group is selected from the group consisting of ester groups, ether groups, thiol groups, carbonyl groups, hydroxyl groups, halogen groups, amide groups, carboxylic groups, imide groups and combinations thereof.

13. The dendrimer according to claim 11, wherein the terminal functional group is at least one member selected from the group consisting of labels, drugs, or probe molecules.

14. The dendrimer according to claim 13, wherein the labels are selected from the group consisting of fluorophores, fluorine, biotin, radioisotope labels, enzyme labels, dyes, chemiluminiscence labels, antigens and antibody labels.

15. The dendrimer according to claim 13, wherein the drugs are selected from the group consisting of antibiotics, analgesic, antibodies; cancer drugs, antiviral, metal chelates, proteins, hormones and nucleic acids.

16. A delivery device for the delivery of a therapeutic agent, wherein the delivery device is a dendrimer according to claim 1, wherein the therapeutic agent is attached to at least one of the periphery ends.

17. The delivery device according to claim 16, wherein the therapeutic agent is selected from the group consisting of antibiotics, analgesic, antibodies; cancer drugs, antiviral, metal chelates, proteins, hormones and nucleic acids.

18. A method for synthesizing a dendrimer comprising a generation (G) branching structure comprising functional terminal groups positioned on the periphery ends, wherein the method comprises:

reacting the functional terminal groups with first branching units to create first larger units, wherein focal points of these larger units are activated for attachments to second branching units to provide second larger units; and repeating such activation and attachment steps until attachment of final branching units to a core thereby completing synthesis of the dendrimer with n layers, wherein n is defined as a value of $1 \leq n \leq G$ and a is a branch multiplier for growing the number of branches, wherein the second branching units are exponentially longer than the first branching units and each subsequent branching units are exponentially longer than previous branching units, wherein each branching unit comprises branching bonds defined by the formula $l_{n-1} = b \times l_n$, wherein $l_n$ is the number of bonds between the nth layer and n−1 layer and b is the branch length multiplier for growth of the length of the branches and wherein the branch length multiplier b satisfies $1 \leq b \leq a$.

\* \* \* \* \*